US010538557B2

(12) United States Patent
Langedijk

(10) Patent No.: US 10,538,557 B2
(45) Date of Patent: Jan. 21, 2020

(54) STABILIZED VIRAL CLASS I FUSION PROTEINS

(71) Applicant: Janssen Vaccines & Prevention B.V., Leiden (NL)

(72) Inventor: Johannes Petrus Maria Langedijk, Amsterdam (NL)

(73) Assignee: Janssen Vaccines & Prevention B.V., Leiden (NL)

( * ) Notice: Subject to any disclaimer, the term of this patent is extended or adjusted under 35 U.S.C. 154(b) by 0 days.

(21) Appl. No.: 15/756,800

(22) PCT Filed: Sep. 1, 2016

(86) PCT No.: PCT/EP2016/070654
§ 371 (c)(1),
(2) Date: Mar. 2, 2018

(87) PCT Pub. No.: WO2017/037196
PCT Pub. Date: Mar. 9, 2017

(65) Prior Publication Data

US 2018/0346521 A1 Dec. 6, 2018

Related U.S. Application Data

(60) Provisional application No. 62/213,466, filed on Sep. 2, 2015.

(51) Int. Cl.

| | |
|---|---|
| ***A61K 39/00*** | (2006.01) |
| ***A61K 39/12*** | (2006.01) |
| ***A61K 39/395*** | (2006.01) |
| ***C07K 16/28*** | (2006.01) |
| ***A61K 39/155*** | (2006.01) |
| ***C07K 14/005*** | (2006.01) |
| *A61P 31/22* | (2006.01) |
| *A61P 31/18* | (2006.01) |
| *A61P 31/16* | (2006.01) |
| *C12N 7/00* | (2006.01) |

(52) U.S. Cl.
CPC ............ *C07K 14/005* (2013.01); *A61P 31/16* (2018.01); *A61P 31/18* (2018.01); *A61P 31/22* (2018.01); *C12N 7/00* (2013.01); *C12N 2740/16022* (2013.01); *C12N 2760/14122* (2013.01); *C12N 2760/16122* (2013.01)

(58) Field of Classification Search
CPC ................ A61K 39/12; C07K 2319/00; C07K 16/3007; B82Y 10/00; B82Y 5/00
See application file for complete search history.

(56) References Cited

FOREIGN PATENT DOCUMENTS

| | | | |
|---|---|---|---|
| EP | 2873423 A2 | | 5/2015 |
| EP | 3072901 A1 | | 9/2016 |
| WO | 2013079473 A1 | | 6/2013 |
| WO | 2014174018 A1 | | 10/2014 |
| WO | WO2014174018 | * | 10/2014 |

OTHER PUBLICATIONS

Singh et al., "LearnCoil-VMF: Computational evidence for coiled-coil-like motifs i many viral membrane-fusion proteins" JMB, 1999, 290:1031-1041.*
Pancera et al. "Structure and immune recognition of trimeric pre-fusion HIV-1 Env," Nature, vol. 514, pp. 455-478 (2014).
Qiao et al. "Specific Single or Double Proline Substitutions in the "Spring-loaded" Coiled-Coil Region of the Influenza Hemagglutinin Impair or Abolish Membrane Fusion Activity," The Journal of Cell Biology, vol. 141, No. 6, pp. 1335-1347 (1998).
Sanders et al. "Stabilization of the soluble, cleaved, trimeric form of the envelope glycoprotein complex of human immunodeficiency virus type 1," Journal of Virology, American Society for Microbiology, vol. 76, No. 17, pp. 8875-8889 (2002).
Singh et al. "LearnCoil-VMF: computational evidence for coiled-coil-like motifs in many viral membrane-fusion proteins," Journal of Molecular Biology, vol. 290, pp. 1031-1041 (1999).
Timmins et al. "Structural studies on the Ebola virus matrix protein VP40 indicate that matrix proteins of enveloped RNA viruses are analogues but not homologues," FEMS Microbiology Letters, vol. 233, pp. 179-186 (2004).
Jardetzky et al. "Activation of paramyxovirus membrane fusion and virus entry," Current Opinion in Virology, pp. 24-33 (2014).
Beddows et al. "Construction and Characterization of Soluble, Cleaved, and Stabilized Trimeric Env Proteins Based on HIV Type 1 Env Subtype A," AIDS Research and Human Retroviruses, vol. 22, No. 6, pp. 569-579 (2006).
Gómara et al. "Roles of a conserved proline in the internal fusion peptide of Ebola glycoprotein," FEBS Letters, vol. 569, pp. 261-266 (2004).
Gruenke et al. "New insights into the spring-loaded conformational change of influenza virus hemagglutinin," Journal of Virology, American Society for Mircrobiology, vol. 76, No. 9, pp. 4456-4466 (2002).
Hunt et al. "Filovirus Entry: A Novelty in the Viral Fusion World," Viruses, vol. 4, pp. 258-275 (2012).
Kang et al. "Structural and immunogenicity studies of a cleaved, stabilized envelope trimer derived from subtype A HIV-1," Vaccine, vol. 27, pp. 5120-5132 (2009).
Krarup et al. "A highly stable prelusion RSV F vaccine derived from structural analysis of the fusion mechanism," Nature Communications, pp. 1-12 (2015).
Search Report and Written Opinion dated Dec. 13, 2016 in International Application No. PCT/EP2016/070654.
Earp et al. "The Many Mechanisms of Viral Membrane Fusion Proteins," Membrane Trafficking in Viral Replication. Current Topics in Microbiology and Immunology, vol. 285. pp. 25-66 (2004).

* cited by examiner

*Primary Examiner* — Barry A Chestnut
(74) *Attorney, Agent, or Firm* — Panitch Schwarze Belisario & Nadel LLP

(57) ABSTRACT

Stable pre-fusion class I fusion proteins in the pre-fusion conformation, including one or more mutations in the hinge-loop that is present between the base helix and the RR1, are described.

25 Claims, 8 Drawing Sheets

Specification includes a Sequence Listing.

Fig. 7A
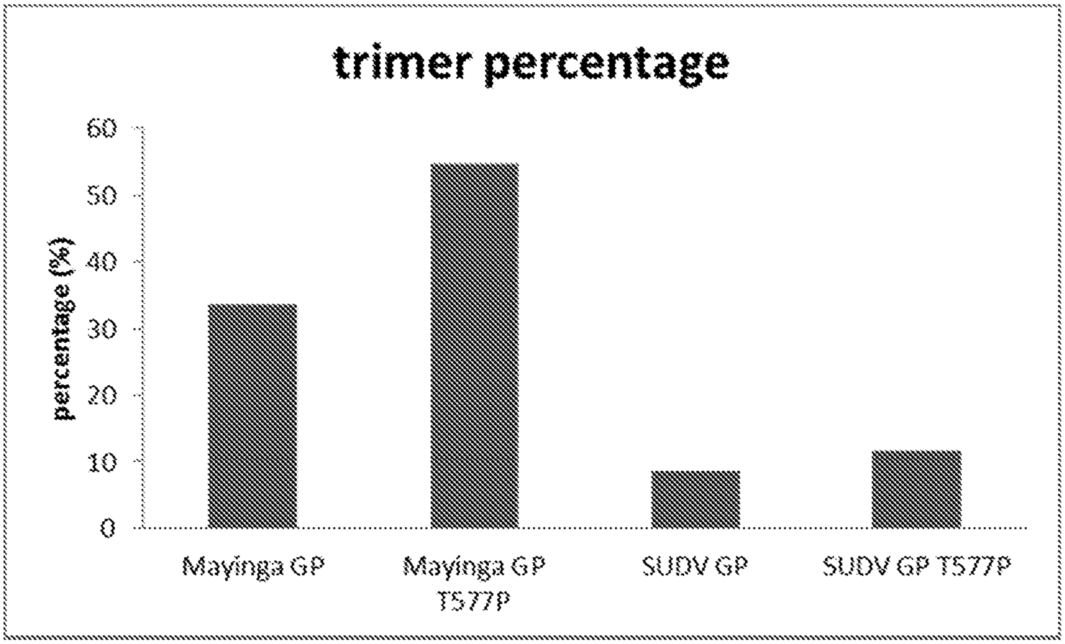
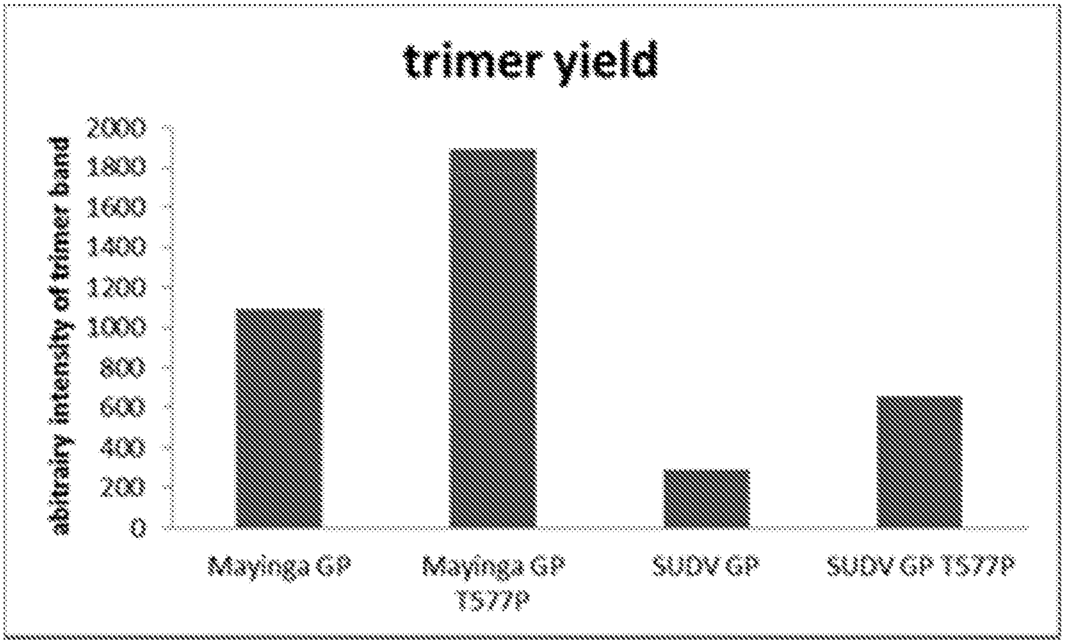
Fig. 7B

Fig. 8A
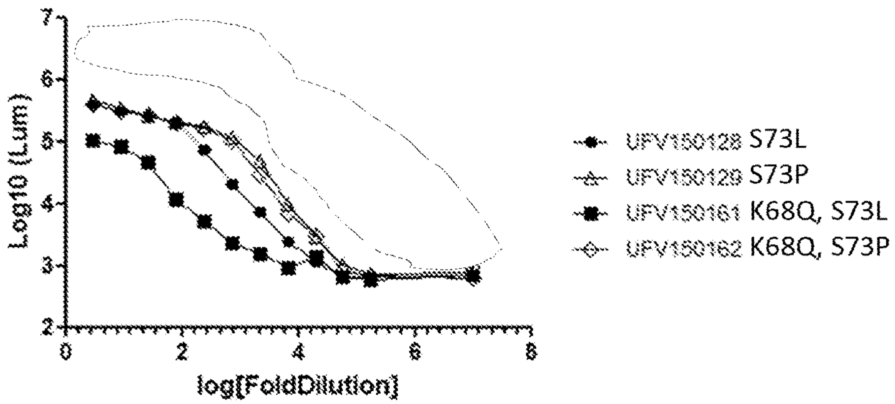
Fig. 8B
| Construct | Description | Expression | Binding CR9114 | Binding CR6261 | Binding CR14045 | Multimer ELISA |
|---|---|---|---|---|---|---|
| UFV150128 | S73L | - | - | - | - | 3.02 |
| UFV150129 | S73P | + | + | + | + | 3.71 |
| UFV150161 | K68Q, S73L | - | - | - | - | **2.00** |
| UFV150162 | K68Q, S73P | ++ | + | + | + | **3.64** |
Fig. 8C
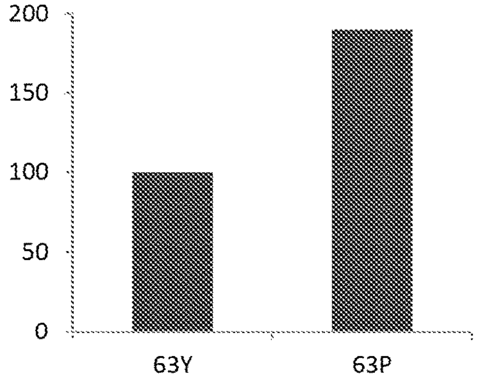

STABILIZED VIRAL CLASS I FUSION PROTEINS

The present invention relates to the field of medicine. The invention in particular relates to recombinant pre-fusion class I fusion proteins and uses thereof, e.g. in immunogenic compositions.

BACKGROUND OF THE INVENTION

Viral fusion proteins are dynamic fusion machines that drive membrane fusion by irreversible protein refolding from a metastable pre-fusion conformation to a stable post-fusion conformation. The fusogenicity of the protein is important for viral infection.

The fusion proteins of enveloped viruses can be classified in different types based on the general irreversible folding mechanism they display to drive fusion of the virus with the target cell. Fusion proteins from unrelated viruses, such as the fusion protein F from Paramyxoviridae, Ebola GP, Retroviridae envelope protein, Coronaviridae spike, Herpesviridea gB, Orthomyxovirideae Hemagglutinin (HA) and Hemagglutinin Esterase (HE), and others are classified as class I fusion proteins and refold from a labile pre-fusion state to a stable post-fusion state through a similar mechanism although they do not exhibit any significant sequence homologies. Class I fusion proteins thus fuse the viral and host-cell membranes by irreversible protein refolding from the labile pre-fusion conformation to the stable post-fusion conformation. Structures have been determined for a variety of class I fusion proteins in pre-fusion conformation and post-fusion conformation providing insight into the mechanism of this complex fusion machine.

Except for Ebola GP and herpes gB, typically, the inactive mature class I fusion protein (e.g. $F_0$ for paramyxoviruses, HA for Orthomyxoviruses) requires cleavage during intracellular maturation, often by a furin-like protease that results in an N-terminal part and an C-terminal part. The cleavage site is near or adjacent to a stretch of 20-25 hydrophobic amino acids (the fusion peptide), followed by a heptad repeat region in the C-terminal part. Since these are class I membrane proteins, the C-terminus contains the transmembrane domain (TM) and after cleavage the membrane bound C-terminal part exposes the N-terminal hydrophobic fusion peptide (FP) (FIG. 1). In order to refold from the pre-fusion to the post-fusion conformation, there are two regions that need to refold, which are referred to as the refolding region 1 (RR1) and refolding region 2 (RR2). For all class I fusion proteins, the RR1 includes the FP and heptad repeat A (HRA). After a trigger, the HRA's of all three protomers in the trimer transform from a helix, or from an assembly of loops and secondary structures, to a long continuous trimeric helical coiled coil (FIG. 1). The FP, located at the N-terminal segment of RR1, is then able to extend away from the viral membrane and inserts in the proximal membrane of the target cell. Next, the refolding region 2 (RR2), which is located C-terminal to RR2 closer to the TM and often includes the heptad repeat B (HRB), relocates to the other side of the fusion protein and binds the HRA coiled-coil trimer with the HRB domain to form the six-helix bundle (6HB) or with an extended polypeptide chain like Influenza HA. These similarities have been recognized by a nomenclature that places viral fusion proteins with these sequence and structural features into the so-called class I viral fusion protein group (Earp et al. Current topics in microbiology and immunology 185: 26-66, (2005); Jardetzky et al. Current opinion in virology 5: 24-33 (2014)).

When viral fusion proteins are used as a vaccine component the fusogenic function is not important. In fact, only the mimicry of the component is important to induce cross reactive antibodies that can bind the virus. Therefore, for development of robust efficacious vaccine components it is desirable that the meta-stable fusion proteins are maintained in their pre-fusion conformation. A stabilized fusion protein in the pre-fusion conformation can induce an efficacious immune response.

SUMMARY OF THE INVENTION

The present invention provides stable, recombinant, class I fusion proteins stabilized in the pre-fusion conformation. In certain embodiments, the pre-fusion polypeptides are soluble.

The invention also provides nucleic acid molecules encoding the pre-fusion polypeptides according to the invention and vectors comprising such nucleic acid molecules.

The invention also relates to compositions, preferably immunogenic compositions, comprising a class I pre-fusion polypeptide, a nucleic acid molecule and/or a vector, and to the use thereof for inducing an immune response against the class I fusion protein, in particular to the use thereof as a vaccine.

The invention also relates to methods for inducing an anti-virus immune response in a subject, comprising administering to the subject an effective amount of a pre-fusion polypeptide, a nucleic acid molecule encoding said polypeptide, and/or a vector comprising said nucleic acid molecule. Preferably, the induced immune response is characterized by neutralizing antibodies to the virus and/or protective immunity against said virus infection. In particular aspects, the invention relates to a method for inducing neutralizing anti-viral antibodies in a subject, comprising administering to the subject an effective amount of an immunogenic composition comprising a pre-fusion polypeptide, a nucleic acid molecule encoding said polypeptide, and/or a vector comprising said nucleic acid molecule.

BRIEF DESCRIPTION OF THE FIGURES

FIG. 7: A) Trimer percentage based on bands obtained with NativePAGE analysis of soluble GPs of Ebola strains Mayinga and Sudan Gulu and the variant with a substitution in the hinge loop at position 577 to Proline. B) relative trimer yield of the different soluble GPs based on NativePAGE.

FIG. 8: A) Multimer-specific binding of Influenza mini-HA variants with either Proline or Leucine at position 73 in the hinge-loop. B) Overview of expression levels, binding to broadly neutralizing antibodies and trimer binding (as shown in A) of the mini-HA variants. C) Multimer content of mini-HA variant with Tyr or Pro at position 63 shown as percentage of multimer content of 63P vs control with 63Y.

DETAILED DESCRIPTION OF THE INVENTION

Virus-cell fusion is the means by which all enveloped viruses, including human pathogens such as for example the influenza virus, the human immunodeficiency virus (HIV) and Ebola virus, enter cells and initiate disease-causing cycles of replication. Virus-cell fusion is executed by one or more viral surface glycoproteins, including one that is generally denoted as the fusion protein. The fusion proteins of enveloped viruses can be classified in different types based on their general irreversible folding mechanism. Thus, fusion proteins from unrelated viruses, such as the fusion protein F from Paramyxoviridae, Ebola GP, Retroviridae envelope protein, Orthomyxoviridea Hemagglutinin (HA) and Hemagglutinin Esterase (HE) are classified as class I fusion proteins. Class I fusion proteins fuse the viral and host-cell membranes by irreversible protein refolding from the labile pre-fusion conformation to the stable post-fusion conformation.

Other known class I fusion proteins are for example the GP protein of Arenaviridae, the E1/E2 protein of Togaviridae, the E protein of Flaviviridae, E(TBEV), E1/E2 (HCV), the GN/GC protein of Bunyaviridae, the G protein of Rhabdoviridae, and the gB, gD, gH protein of Herpesviridae.

Figure 1:
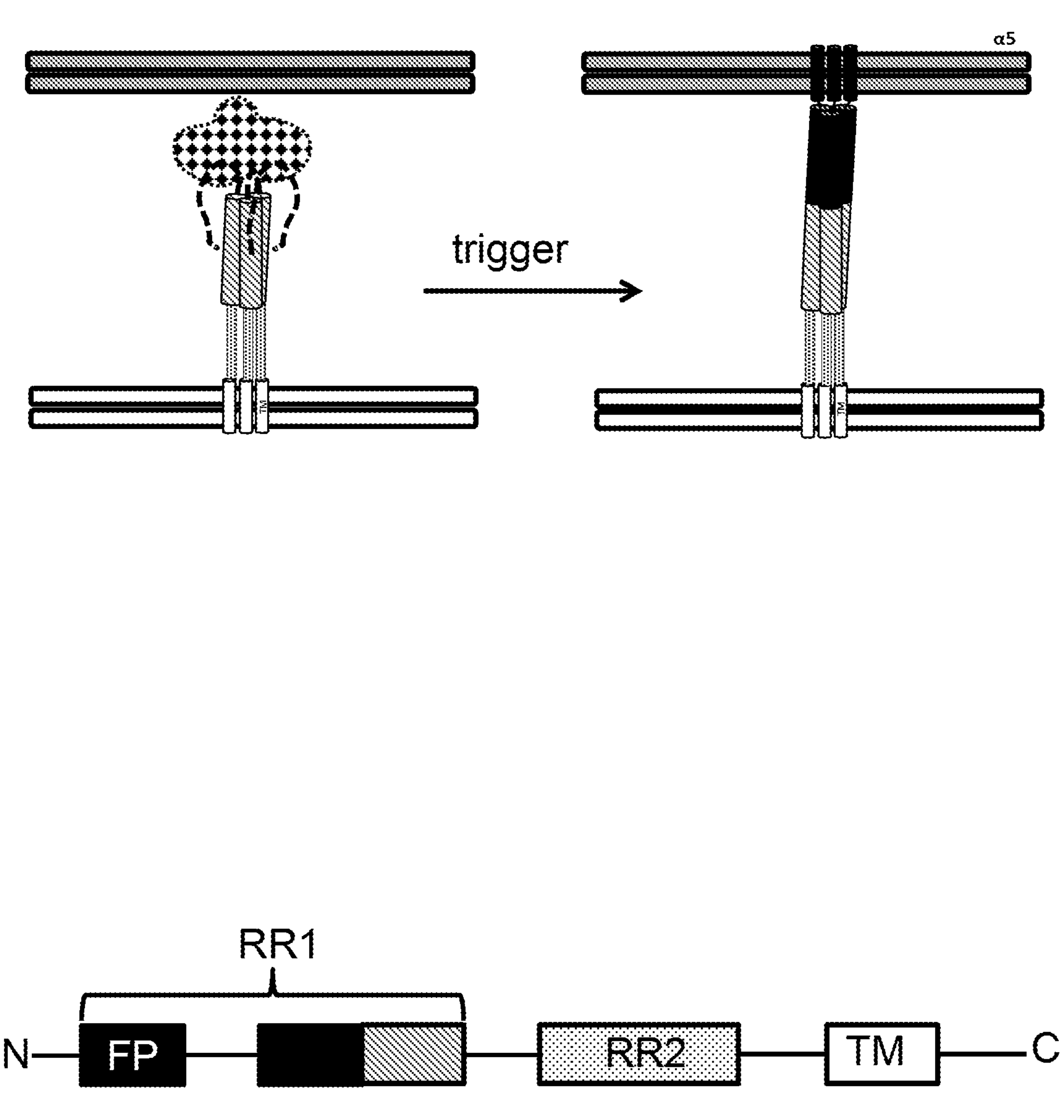
FIG. 1: Cartoon of fusion protein trimer in pre-fusion conformation (top left) and in the intermediate state (top right) and schematic representation of the conserved elements of fusion domain of class I fusion proteins (bottom). Fusion peptide (FP), refolding region 1 (RR1), refolding region 2 (RR2) and transmembrane region (TM) are indicated. Molecular structures of fusion proteins are very diverse and may contain a separate receptor binding domain (top left, checkered), however all fusion proteins contain a recognizable fusion domain (diagonal fill, black fill). Generally, the FP is followed by a heptad repeat region in the C-terminal part (black and diagonal striped fill) which both form the RR1. After a trigger, the N-terminal part of RR1 (black) which is connected to the base helix (diagonal fill) via a hinge loop is assembled on the base helix to form a long continuous helical coiled coil. The post-fusion form of the fusion protein is formed when refolding region 2 binds the refolded RR1. Since these are class I membrane proteins, the C-terminus contains the transmembrane domain (TM).

All class I fusion proteins typically comprise the same structural features (see FIG. 1). The refolding region 1 (RR1) includes the fusion peptide (FP) and heptad repeat A (HRA). After a trigger, the HRA's and FP's of all three protomers in the trimer transform from a helix, or form an assembly of loops and secondary structures, to a long continuous trimeric helical coiled coil (FIG. 1). The FP, located at the N-terminal segment of RR1, is then able to extend away from the viral membrane and inserts in the proximal membrane of the target cell. Next, the refolding region 2 (RR2), which is located C-terminal to RR2 closer to the TM and often includes the heptad repeat B (HRB), relocates to the other side of the fusion protein and binds the HRA coiled-coil trimer with the HRB domain to form the six-helix bundle or with an extended polypeptide chain like influenza HA. These similarities have been recognized by a nomenclature that places viral fusion proteins with these sequence and structural features into the so-called class I viral fusion protein group (Earp et al. Current topics in microbiology and immunology 185: 26-66, (2005); Jardetzky et al. Current opinion in virology 5: 24-33 (2014).

Although the formation of the RR1 coiled coil and the relocation of RR2 to complete the 6 helix bundle are the fundamental similarities, the divergence in the fusion mechanism is great. The structural studies of several class I fusion proteins showed that they represent very distinct structural subfamilies. The overall folding of the fusion proteins and the trigger for unfolding is different for the family members and the sequence of events may differ for each class I fusion protein. For instance, for many paramyxoviruses it is proposed that the HRB will be exposed and released before the release and formation of the HRA domain.

Figure 2:
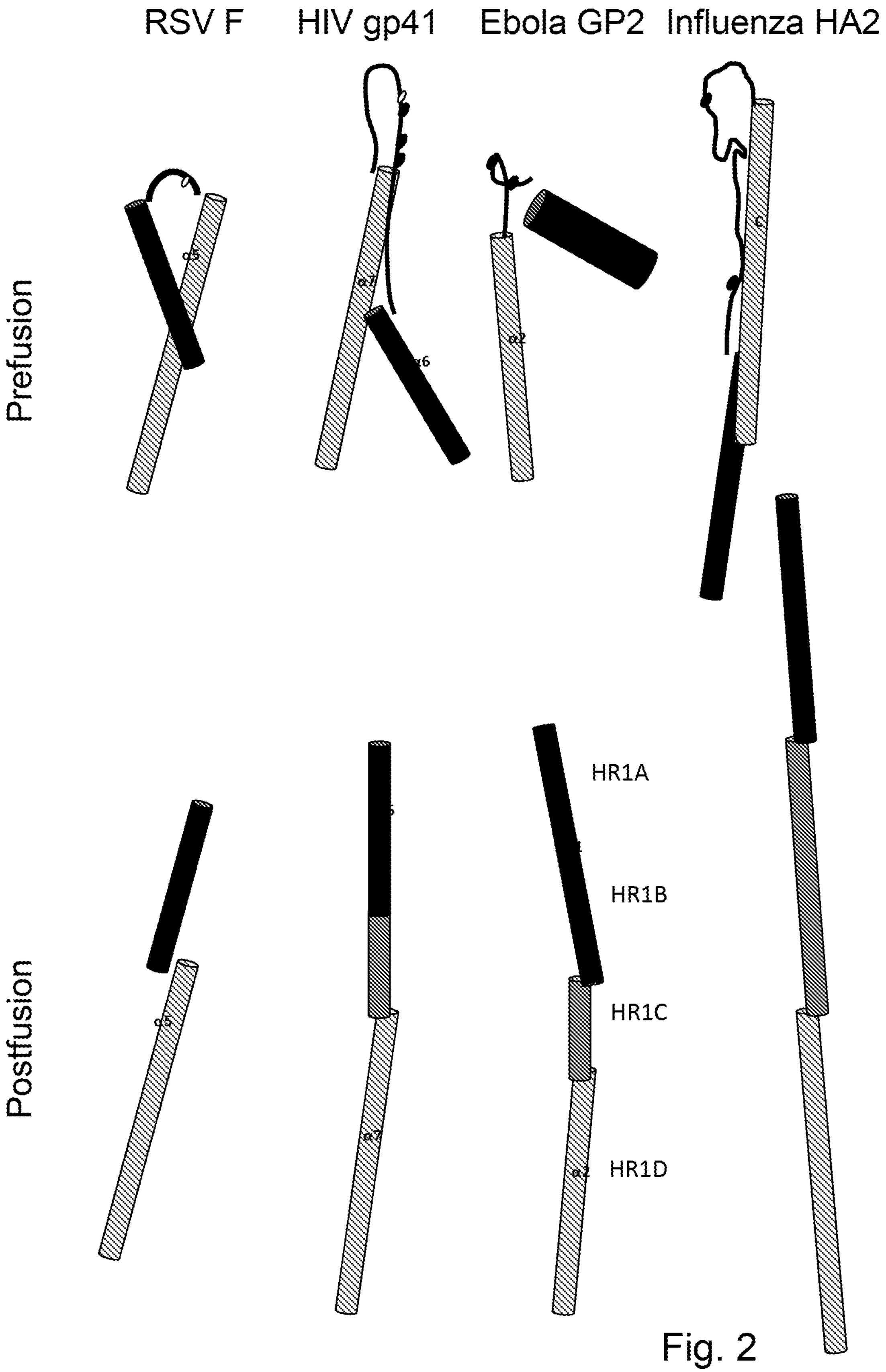
FIG. 2: Cartoons of a fragment of RR1 (black), hinge loop and base helix (diagonal striped fill) for several class I fusion proteins in the pre-fusion (top row) and post-fusion conformation (bottom row). After a trigger, the N-terminal part of RR1 (black fill) which is connected to the base helix (diagonal striped fill) via a hinge loop (top) is assembled on the base helix to form a long continuous helix (bottom). The small white circles in the hinge of RSV F and HIV gp41 represent substitutions to proline that stabilize the pre-fusion conformation. The small black circles are potential positions which are structurally homologous to the white circles and potential positions for stabilizing substitutions.

Apart from the RR1 and RR2, all known class I fusion proteins share another distinctive structural feature, which is referred to herein as the base helix. The base helix is a part of the dynamic fusion protein that does not change conformation during the transformation from the pre to post-fusion conformation. The base helix is at the heart of the fusion protein and forms a trimeric helical base. After the trigger and the initiation of the refolding, the trimeric helical base is extended by assembly of the first helix of RR1. In respiratory syncytial virus fusion protein (RSV F), the base helix is helix alpha 5. After refolding, helix α4 is the first structural element that assembles on top of the structurally conserved, preformed α5 helix base. The flexible α4-α5 loop is an important structural element because it is the first region in this dynamic protein that needs to hinge in order to achieve the assembly of α4 on top of the α5 (FIG. 2).

In the research that led to the present invention, it was discovered that hydrophobic residues, and in particular a proline (Pro) substitution in this hinge loop can stabilize the loop. Stability is obtained by hydrophobic interactions but especially by the rigidity of the proline which limits the backbone conformations of the peptide chain in the hinge region. The proline substitution in this critical hinge region stabilized the pre-fusion conformation of RSV F by restricting the hinge movement and obstructing the movement and assembly of helix 4 on top of helix 5. Surprisingly, also for HIV a stabilizing proline substitution in the hinge loop has been described (Sanders et al. Journal of virology 76, 8875-8889 (2002)).

Recently the crystal structure of the pre-fusion conformation of the fusion domain gp41 of HIV has been solved (Pancera et al. Nature 514, 455-461 (2014)) and by comparing it to the known structure of the gp41 post-fusion 6HB, helix 7 can be identified as the base helix. After refolding of RR1, the hinge loop between α6 and α7 and helix α6 are mounted on top of the base helix α7 to form the long extended coiled coil. Similar to the α4-α5 hinge loop in RSV pre-fusion F, the α6-α7 hinge-loop of pre-fusion HIV gp41 is also the most disordered element of the fusion protein. The gp41 α6-α7 loop is in fact completely disordered and no electron density could be measured in the crystal structure. An important substitution that increased the stability of pre-fusion gp41 is I559P which is located at a structural homologous position as the stabilizing S215P in RSV-F. Although the gp41 I559P is not visible in the structure, the position in the hinge-loop between the base helix and the mounted helix is very similar to position 215 in the hinge-loop of pre-fusion RSV-F (FIG. 2). Although the I559P was designed to destabilize the 6HB post-fusion conformation, the proline at position 559 prevents the hinge movement of the α6-α7 loop in a similar fashion as the proline at position 215 inhibits the hinge movement of the α4-α5 hinge in pre-fusion RSV F (Krarup et al., Nature Communications 8143 (2015), doi:10.1038/ncomms9143). This analogy between two unrelated class I fusion proteins reveals the importance of the hinge as a critical step in refolding of RR1. It also shows that stabilizing the unstable hinge loop is a successful strategy to stabilize the unstable pre-fusion conformation of class I fusion proteins. Introduction of a proline in the hinge loop and preferably relatively close to the base helix thus can be used as a common solution to stabilize the pre-fusion conformation of class I fusion proteins which would make them superior vaccine components.

According to the invention, stabilized hinge loops have been designed for several class I fusion proteins, in particular the class I fusion proteins for which a pre-fusion structure has been elucidated, like influenza HA, retrovirus envelope protein and Ebola GP. For all these examples, it has been shown according to the invention that proline residues in the hinge loop C-terminal to the base helix stabilize the pre-fusion conformation. Therefore, the base helices in the class I fusion proteins were identified and based on the position of the stabilizing proline in RSV F and HIV gp41 hinge loop, the approximate position for a stabilizing proline in the other hinge loops were deduced (FIG. 2 and Table 1).

The present invention thus provides recombinant pre-fusion class I fusion proteins that are stabilized in the pre-fusion conformation. The stable class I pre-fusion proteins of the invention are in the pre-fusion conformation, i.e. they comprise (display) epitopes that is specific to the pre-fusion conformation of the fusion protein. An epitope that is specific to the pre-fusion conformation protein is an epitope that is not presented in the post-fusion conformation. Without wishing to be bound by any particular theory, it is believed that the pre-fusion conformation of class I fusion proteins may contain epitopes that are the same as those on the protein expressed on natural virions, and therefore may provide advantages for eliciting protective neutralizing antibodies. In certain embodiments, the proteins of the invention thus comprise at least one epitope that is recognized by a pre-fusion specific monoclonal antibody.

According to the invention it has been shown that class I fusion proteins can be stabilized in the hinge-loop that is present between the base helix and the RR1 by mutation of one or more specific amino acid residue(s), in particular by mutation of one or more specific hydrophobic amino acid residues into proline (Pro). Table 2 discloses the amino acid sequence of the regions comprising the hinge loop of several class I fusion proteins. The actual hinge loops correspond to the underlined sequences in Table 2.

In certain embodiments, the class I fusion protein is a retroviral envelope protein.

In certain embodiments, the retroviral envelope protein is a HIV-1 envelope protein. In certain embodiments, the hinge loop (underlined) is comprised within the amino acid sequence:

(SEQ ID NO: 1)
540 QARQLLSGIVQQQNNLLRAIEAQQHLLQLTVWGIKQLQARI 580
or (SEQ 2)
539 QARQLLSGIVQQQSNLLRAIEAQQHMLQLTVWGIKQLQTRV 579.

In certain embodiments, the stable HIV-1 envelope protein according to the invention comprises a mutation in the hinge loop of the amino acid residue Leu on position 555, a mutation of amino acid residue Leu on position 556, and/or a mutation of the amino acid residue Ala at position 558.

In certain embodiments, the stable pre-fusion HIV-1 envelope protein according to the invention comprises a mutation in the hinge loop of the amino acid residue Leu on position 555 into Pro, a mutation of the amino acid residue Leu on position 556 into Pro, and/or a mutation of the amino acid residue Ala on position 558 into Pro.

In certain embodiments, the stable pre-fusion HIV-1 envelope protein according to the invention comprises an amino acid sequence selected from the group consisting of:

(SEQ ID NO: 3)
QARQLLSGIVQQQNNPLRAIEAQQHLLQLTVWGIKQLQARI;

(SEQ ID NO: 4)
QARQLLSGIVQQQNNLPRAIEAQQHLLQLTVWGIKQLQARI;

(SEQ ID NO: 5)
QARQLLSGIVQQQNNLLRPIEAQQHLLQLTVWGIKQLQARI;

(SEQ ID NO: 6)
QARQLLSGIVQQQSNPLRAIEAQQHMLQLTVWGIKQLQTRV;

(SEQ ID NO: 7)
QARQLLSGIVQQQSNLPRAIEAQQHMLQLTVWGIKQLQTRV;
and (SEQ ID NO: 8)
QARQLLSGIVQQQSNLLRPIEAQQHMLQLTVWGIKQLQTRV.

It will be understood by the skilled person that the numbering of the amino acid residues relates to the numbering of the amino acid residues in the full-length HIV-1 envelope protein.

In certain embodiments, the present invention thus provides a stable pre-fusion HIV-1 envelope protein comprising an amino acid sequence, wherein the amino acid residue on position 555, 556 and/or 558 is proline.

In certain embodiments, the present invention provides a stable pre-fusion HIV-1 envelope protein comprising the amino acid sequence of SEQ ID NO: 9, wherein the amino acid residue on position 555, 556 and/or 558 is proline.

In certain embodiments, the stable pre-fusion HIV-1 envelope protein further comprises a proline on position 559.

In certain embodiments, the retroviral envelope protein is a HIV-2 envelope protein.

In certain embodiments, the hinge loop (underlined) is comprised within the amino acid sequence:

```
                                       (SEQ ID NO: 30)
538 QSRTLLAGIVQQQQQLLDAVKRQQELLRLTVWGTKNLQSRV 578.
```

In certain embodiments, the stable HIV-2 envelope protein according to the invention comprises a mutation in the hinge loop of the amino acid residue Leu on position 553 and/or a mutation of amino acid residue Leu on position 554, a mutation of amino acid residue Ala at position 556, and/or a mutation of amino acid residue Val at position 557.

In certain embodiments, the stable HIV-2 envelope protein according to the invention comprise a mutation in the hinge loop of the amino acid residue Leu on position 553 into Pro, a mutation of amino acid residue Leu on position 554 into Pro, a mutation of amino acid residue Ala at position 556 into Pro, and/or a mutation of amino acid residue Val at position 557 into Pro.

In certain embodiments, the stable pre-fusion HIV-2 envelope protein according to the invention comprises an amino acid sequence selected from the group consisting of:

```
                                       (SEQ ID NO: 31)
LLAGIVQQQQQPLDAVKRQQELLRLTVWG;

                                       (SEQ ID NO: 32)
LLAGIVQQQQQLPDAVKRQQELLRLTVWG;

                                       (SEQ ID NO: 33)
LLAGIVQQQQQLLDPVKRQQELLRLTVWG;
and

                                       (SEQ ID NO: 34)
LLAGIVQQQQQLLDAPKRQQELLRLTVWG.
```

It will be understood by the skilled person that the numbering of the amino acid residues relates to the numbering of the amino acid residues in the full-length HIV-2 envelope protein.

In certain embodiments, the present invention thus provides a stable pre-fusion HIV-2 envelope protein comprising an amino acid sequence, wherein the amino acid residue on position 553, 554, 556 and/or 557 is proline.

In certain embodiments, the present invention provides a stable pre-fusion HIV-2 envelope protein comprising the amino acid sequence of SEQ ID NO: 35, wherein the amino acid residue on position 553, 554, 556 and/or 557 is proline.

In certain embodiments, the class I fusion protein is a filovirus fusion protein (GP).

In certain embodiments, the filovirus GP protein is an Ebola virus GP protein.

In certain embodiments, the hinge loop (underlined) is comprised within the amino acid sequence 553 GLICGLRQLANETTQALQLFLRAT<u>TELRTF</u>SILNRKAIDFLLQR 596 (SEQ ID NO: 10).

In certain embodiments, the stable Ebolavirus GP protein according to the invention comprises a mutation in the hinge loop of the amino acid residue Thr at position 577, and/or a mutation of the amino acid residue Leu at position 579. In certain embodiments, the stable Ebolavirus GP protein according to the invention comprises a mutation in the hinge loop of the amino acid residue Thr at position 577 into Pro, and/or a mutation of the amino acid residue Leu at position 579 into Pro.

In certain embodiments, the stable Ebolavirus GP protein according to the invention comprises an amino acid sequence selected from the group consisting of:

```
                                       (SEQ ID NO: 11)
GLICGLRQLANETTQALQLFLRATPELRTFSILNRKAIDFLLQR;
and

                                       (SEQ ID NO: 12)
GLICGLRQLANETTQALQLFLRATTEPRTFSILNRKAIDFLLQR.
```

It will be understood by the skilled person that the numbering of the amino acid residues relates to the numbering of the amino acid residues in the full-length Ebola virus GP protein.

In certain embodiments, the present invention thus provides a stable pre-fusion Ebolavirus GP protein, wherein the amino acid residue on position 577 and/or 579 is proline.

In certain embodiments, the present invention provides a stable pre-fusion Ebolavirus GP protein comprising the amino acid sequence of SEQ ID NO: 13, wherein the amino acid residue on position 577 and/or 579 is proline.

In certain embodiments, the filovirus GP protein is a Marburg virus GP protein.

In certain embodiments, the hinge loop (underlined) is comprised within the amino acid sequence 554 NLVCRLRRLANQTAKSLELLLRVT<u>TEERTF</u>SLINRHAIDFLLAR 597 (SEQ ID NO: 14).

In certain embodiments, the Marburg virus GP protein according to the invention comprise a mutation in the hinge loop of the amino acid residue Thr at position 578, and/or a mutation of the amino acid residue Glu at position 580.

In certain embodiments, the Marburg virus GP protein according to the invention comprise a mutation in the hinge loop of the amino acid residue Thr at position 578 into Pro, and/or a mutation of the amino acid residue Glu at position 580 into Pro.

In certain embodiments, the stable Marburg virus GP protein according to the invention comprises an amino acid sequence selected from the group consisting of:

```
                                       (SEQ ID NO: 15)
NLVCRLRRLANQTAKSLELLLRVTPEERTFSLINRHAIDFLLAR;
and

                                       (SEQ ID NO: 16)
NLVCRLRRLANQTAKSLELLLRVTTEPRTFSLINRHAIDFLLAR.
```

It will be understood by the skilled person that the numbering of the amino acid residues relates to the numbering of the amino acid residues in the full-length Marburg virus GP protein.

In certain embodiments, the present invention thus provides a stable pre-fusion Marburg virus GP protein, wherein the amino acid residue on position 578 and/or 580 is proline.

In certain embodiments, the present invention provides a stable pre-fusion Marburg GP protein comprising the amino acid sequence of SEQ ID NO: 17, wherein the amino acid residue on position 578 and/or 580 is proline.

In certain embodiments, the class I fusion protein is an influenza hemagglutinin (HA) protein of an influenza A virus. In certain embodiments, the influenza hemagglutinin (HA) protein is a HA protein of an influenza A virus of phylogenetic group 1. In certain embodiments, the influenza hemagglutinin (HA) protein is a H1 HA protein.

The influenza HA protein is typically composed of a HA' domain (comprising about 329 amino acid residues) and a HA2 domain (comprising about 175 amino acid residues).

In certain embodiments, the hinge loop (underlined) is comprised within the amino acid sequence 38

(SEQ ID NO: 18)
QKSTQNAINGITNKVNSVIEKMNTQFTAVGKEFNKLERRMENLNKKVD
DGFID.

In certain embodiments, the HA protein comprises a mutation in the hinge loop (B-loop) of HA2 of the amino acid residue Phe at position 63 (HA2 numbering) and/or a mutation of the amino acid residue Leu at position 73.

In certain embodiments, the HA protein comprises a mutation in the hinge loop of the amino acid residue Phe at position 63 into Pro, and/or a mutation of the amino acid residue Leu at position 73 into Pro.

In certain embodiments, the stable pre-fusion H1 HA protein according to the invention comprises an amino acid sequence selected from the group consisting of:

(SEQ ID NO: 19)
QKSTQNAINGITNKVNSVIEKMNTQPTAVGKEFNKLERRMENLNKKVDDG
FID;
and (SEQ ID NO: 20)
QKSTQNAINGITNKVNSVIEKMNTQFTAVGKEFNKPERRMENLNKKVDDG
FID.

It will be understood by the skilled person that the numbering of the amino acid residues relates to the numbering of the amino acid residues in the HA2 domain.

In certain embodiments, the present invention thus provides a stable pre-fusion HA protein, wherein the amino acid residue in the HA2 domain on position 63 and/or 73 is proline.

In certain embodiments, the present invention provides a stable pre-fusion HA protein comprising the amino acid sequence of SEQ ID NO: 21, wherein the amino acid residue in the HA2 domain on position 63 and/or 73 is proline.

In certain embodiments, the influenza hemagglutinin (HA) protein is a HA protein of an influenza A virus of phylogenetic group 2. In certain embodiments, the influenza hemagglutinin (HA) protein is a H3 HA protein.

In certain embodiments, the hinge loop (underlined) is comprised within the amino acid sequence (SEQ ID NO: 22)
47 KSTQAAINQINGKLNRLIGKTNEKFHQIEKEFSEVEGRIQDLEKYV
EDTKID.

In certain embodiments, the stable influenza HA protein comprises a mutation in the hinge loop (B-loop) of HA2 of the amino acid residue Phe at position 72 and/or a mutation of the amino acid residue Val at position 82.

In certain embodiments, the stable influenza HA protein comprises a mutation in the hinge loop (B-loop) of HA2 of the amino acid residue Phe at position 72 into Pro and/or a mutation of the amino acid residue Val at position 82 into Pro.

In certain embodiments, the stable pre-fusion H3 HA protein according to the invention comprises an amino acid sequence selected from the group consisting of:

(SEQ ID NO: 23)
LKSTQAAINQINGKLNRLIGKTNEKPHQIEKEFSEVEGRIQDLEKYVEDT
KID;
and (SEQ ID NO: 24)
LKSTQAAINQINGKLNRLIGKTNEKFHQIEKEFSEPEGRIQDLEKYVEDT
KID.

It will be understood by the skilled person that the numbering of the amino acid residues relates to the numbering of the amino acid residues in the HA2 domain.

In certain embodiments, the present invention thus provides a stable pre-fusion HA protein, wherein the amino acid residue in the HA2 domain on position 72 and/or 82 is proline.

In certain embodiments, the present invention provides a stable pre-fusion HA protein comprising the amino acid sequence of SEQ ID NO: 25, wherein the amino acid residue on position 72 and/or 82 is proline.

In certain embodiments, the class I fusion polypeptide is an influenza hemagglutinin (HA) polypeptide of an influenza B virus.

In certain embodiments, the hinge loop is comprised within the amino acid sequence (SEQ ID NO: 26)
LKSTQEAINKITKNLNSLELEVKNLQRLSGAMDELHNEILELDEKVDD
LRAD.

In certain embodiments, the stable HA polypeptides comprise a mutation in the hinge loop (B-loop) of HA2 of the amino acid residue Leu at position 62 and/or a mutation of the amino acid Leu at position 72.

In certain embodiments, the stable HA polypeptides comprise a mutation in the hinge loop (B-loop) of HA2 of the amino acid residue Leu at position 62 into Pro and/or a mutation of the amino acid Leu at position 72 into Pro.

In certain embodiments, the stable pre-fusion B HA protein according to the invention comprises an amino acid sequence selected from the group consisting of:

(SEQ ID NO: 27)
LKSTQEAINKITKNLNSLELEVKNPQRLSGAMDELHNEILELDEKVDDL
RAD;
and (SEQ ID NO: 28)
LKSTQEAINKITKNLNSLELEVKNLQRLSGAMDEPHNEILELDEKVDDL
RAD.

It will be understood by the skilled person that the numbering of the amino acid residues relates to the numbering of the amino acid residues in the full-length influenza B virus HA2 protein.

In certain embodiments, the present invention thus provides a stable pre-fusion HA protein, wherein the amino acid residue on position 62 and/or 72 of HA2 is proline.

In certain embodiments, the present invention provides a stable pre-fusion HA protein comprising the amino acid sequence of SEQ ID NO: 29, wherein the amino acid residue on position 62 and/or 72 of HA2 is proline.

According to the invention, the stable pre-fusion class I proteins thus comprise at least one stabilizing mutation in the hinge loop as compared to the wild-type class I fusion. As used throughout the present application, the amino acid positions are given in reference to the sequence of the full length class I fusion protein (or in reference to the HA2 domain for the influenza HA proteins). Sequence alignments can be done using methods well known in the art, e.g. by CLUSTALW, Bioedit or CLC Workbench.

An amino acid according to the invention can be any of the twenty naturally occurring (or 'standard' amino acids) or variants thereof, such as e.g. D-amino acids (the D-enantiomers of amino acids with a chiral center), or any variants that are not naturally found in proteins, such as e.g. norleucine. The standard amino acids can be divided into several groups based on their properties. Important factors are charge, hydrophilicity or hydrophobicity, size and functional groups. These properties are important for protein structure and protein-protein interactions. Some amino acids have special properties such as cysteine, that can form covalent disulfide bonds (or disulfide bridges) to other cysteine residues, proline that induces turns of the polypeptide backbone, and glycine that is more flexible than other amino acids. Table 1 shows the abbreviations and properties of the standard amino acids.

In certain embodiments, the stable pre-fusion class I proteins are full length.

In certain embodiments, the stable pre-fusion class I proteins are soluble proteins. for example soluble proteins based on the ectodomain or subdomains of the ectodomain.

It will be appreciated by a skilled person that the mutations can be made to the protein by routine molecular biology procedures. The mutations according to the invention preferably result in increased expression levels and/or increased stabilization of the pre-fusion class I polypeptides as compared to the class I fusion polypeptides that do not comprise these mutation(s).

The pre-fusion class I fusion protein polypeptides according to the invention are stable, i.e. do not readily change into the post-fusion conformation upon processing of the polypeptides, such as e.g. purification, freeze-thaw cycles, and/or storage etc.

In certain embodiments, the pre-fusion class I fusion protein polypeptides according to the invention have an increased stability upon storage a 4° C. as compared to a class I fusion protein polypeptide without the mutation(s). In certain embodiments, the polypeptides are stable upon storage at 4° C. for at least 30 days, preferably at least 60 days, preferably at least 6 months, even more preferably at least 1 year.

In certain embodiments, the class I fusion protein polypeptides according to the invention have an increased stability when subjected to heat, as compared to class I fusion protein polypeptides without said mutation(s). In certain embodiments, the pre-fusion conformation of the class I fusion protein polypeptides are heat stable for at least 30 minutes at a temperature of 55° C., preferably at 58° C., more preferably at 60° C. With "heat stable" it is meant that the polypeptides still display the at least one pre-fusion specific epitope after having been subjected for at least 30 minutes to an increased temperature (i.e. a temperature of 55° C. or above.

In certain embodiments, the proteins display the at least one pre-fusion specific epitope after being subjected to 1 to 6 freeze-thaw cycles in an appropriate formulation buffer.

As used throughout the present application nucleotide sequences are provided from 5' to 3' direction, and amino acid sequences from N-terminus to C-terminus, as custom in the art.

The present invention further provides nucleic acid molecules encoding the pre-fusion class I proteins according to the invention.

In preferred embodiments, the nucleic acid molecules encoding the proteins according to the invention are codon-optimized for expression in mammalian cells, preferably human cells. Methods of codon-optimization are known and have been described previously (e.g. WO 96/09378). A sequence is considered codon-optimized if at least one non-preferred codon as compared to a wild type sequence is replaced by a codon that is more preferred. Herein, a non-preferred codon is a codon that is used less frequently in an organism than another codon coding for the same amino acid, and a codon that is more preferred is a codon that is used more frequently in an organism than a non-preferred codon. The frequency of codon usage for a specific organism can be found in codon frequency tables, such as in website: www.kazusa.or.jp/codon. Preferably more than one non-preferred codon, preferably most or all non-preferred codons, are replaced by codons that are more preferred. Preferably the most frequently used codons in an organism are used in a codon-optimized sequence. Replacement by preferred codons generally leads to higher expression.

It will be understood by a skilled person that numerous different polynucleotides and nucleic acid molecules can encode the same polypeptide as a result of the degeneracy of the genetic code. It is also understood that skilled persons may, using routine techniques, make nucleotide substitutions that do not affect the polypeptide sequence encoded by the nucleic acid molecules to reflect the codon usage of any particular host organism in which the polypeptides are to be expressed. Therefore, unless otherwise specified, a "nucleotide sequence encoding an amino acid sequence" includes all nucleotide sequences that are degenerate versions of each other and that encode the same amino acid sequence. Nucleotide sequences that encode proteins and RNA may or may not include introns.

Nucleic acid sequences can be cloned using routine molecular biology techniques, or generated de novo by DNA synthesis, which can be performed using routine procedures by service companies having business in the field of DNA synthesis and/or molecular cloning (e.g. GeneArt, GenScripts, Invitrogen, Eurofins).

The invention also provides vectors comprising a nucleic acid molecule as described above. In certain embodiments, a nucleic acid molecule according to the invention thus is part of a vector. Such vectors can easily be manipulated by methods well known to the person skilled in the art, and can for instance be designed for being capable of replication in prokaryotic and/or eukaryotic cells. In addition, many vectors can be used for transformation of eukaryotic cells and will integrate in whole or in part into the genome of such cells, resulting in stable host cells comprising the desired nucleic acid in their genome. The vector used can be any vector that is suitable for cloning DNA and that can be used for transcription of a nucleic acid of interest. Suitable vectors according to the invention are e.g. adenovectors, such as e.g. Ad26 or Ad35, alphavirus, paramyxovirus, vaccinia virus, herpes virus, retroviral vectors etc. The person skilled in the art is capable of choosing suitable expression vectors, and inserting the nucleic acid sequences of the invention in a functional manner.

Host cells comprising the nucleic acid molecules encoding the pre-fusion class I proteins form also part of the invention. The pre-fusion class I proteins may be produced through recombinant DNA technology involving expression of the molecules in host cells, e.g. Chinese hamster ovary (CHO) cells, tumor cell lines, BHK cells, human cell lines such as HEK293 cells, PER.C6 cells, or yeast, fungi, insect cells, and the like, or transgenic animals or plants. In certain embodiments, the cells are from a multicellular organism, in certain embodiments they are of vertebrate or invertebrate origin. In certain embodiments, the cells are mammalian cells. In certain embodiments, the cells are human cells. In general, the production of a recombinant proteins, such the pre-fusion class I proteins of the invention, in a host cell comprises the introduction of a heterologous nucleic acid molecule encoding the class I proteins in expressible format into the host cell, culturing the cells under conditions conducive to expression of the nucleic acid molecule and allowing expression of the polypeptide in said cell. The nucleic acid molecule encoding a protein in expressible format may be in the form of an expression cassette, and usually requires sequences capable of bringing about expression of the nucleic acid, such as enhancer(s), promoter, polyadenylation signal, and the like. The person skilled in the art is aware that various promoters can be used to obtain expression of a gene in host cells. Promoters can be constitutive or regulated, and can be obtained from various sources, including viruses, prokaryotic, or eukaryotic sources, or artificially designed.

Cell culture media are available from various vendors, and a suitable medium can be routinely chosen for a host cell to express the protein of interest, here the pre-fusion class I proteins. The suitable medium may or may not contain serum.

A "heterologous nucleic acid molecule" (also referred to herein as 'transgene') is a nucleic acid molecule that is not naturally present in the host cell. It is introduced into for instance a vector by standard molecular biology techniques. A transgene is generally operably linked to expression control sequences. This can for instance be done by placing the nucleic acid encoding the transgene(s) under the control of a promoter. Further regulatory sequences may be added. Many promoters can be used for expression of a transgene(s), and are known to the skilled person, e.g. these may comprise viral, mammalian, synthetic promoters, and the like. A non-limiting example of a suitable promoter for obtaining expression in eukaryotic cells is a CMV-promoter (U.S. Pat. No. 5,385,839), e.g. the CMV immediate early promoter, for instance comprising nt. −735 to +95 from the CMV immediate early gene enhancer/promoter. A polyadenylation signal, for example the bovine growth hormone polyA signal (U.S. Pat. No. 5,122,458), may be present behind the transgene(s). Alternatively, several widely used expression vectors are available in the art and from commercial sources, e.g. the pcDNA and pEF vector series of Invitrogen, pMSCV and pTK-Hyg from BD Sciences, pCMV-Script from Stratagene, etc, which can be used to recombinantly express the protein of interest, or to obtain suitable promoters and/or transcription terminator sequences, polyA sequences, and the like.

The cell culture can be any type of cell culture, including adherent cell culture, e.g. cells attached to the surface of a culture vessel or to microcarriers, as well as suspension culture. Most large-scale suspension cultures are operated as batch or fed-batch processes because they are the most straightforward to operate and scale up. Nowadays, continuous processes based on perfusion principles are becoming more common and are also suitable. Suitable culture media are also well known to the skilled person and can generally be obtained from commercial sources in large quantities, or custom-made according to standard protocols. Culturing can be done for instance in dishes, roller bottles or in bioreactors, using batch, fed-batch, continuous systems and the like. Suitable conditions for culturing cells are known (see e.g. Tissue Culture, Academic Press, Kruse and Paterson, editors (1973), and R. I. Freshney, Culture of animal cells: A manual of basic technique, fourth edition (Wiley-Liss Inc., 2000, ISBN 0-471-34889-9)).

The invention further provides compositions comprising a pre-fusion class I protein and/or a nucleic acid molecule, and/or a vector, as described above. The invention thus provides compositions comprising a pre-fusion class I protein that displays an epitope that is present in a pre-fusion conformation of the class I protein but is absent in the post-fusion conformation. The invention also provides compositions comprising a nucleic acid molecule and/or a vector, encoding such pre-fusion class I protein. The invention further provides immunogenic compositions comprising a pre-fusion class I protein, and/or a nucleic acid molecule, and/or a vector, as described above. The invention also provides the use of a stabilized pre-fusion class I protein, a nucleic acid molecule, and/or a vector, according to the invention, for inducing an immune response against said class I proteins in a subject. Further provided are methods for inducing an immune response against a class I fusion protein in a subject, comprising administering to the subject a pre-fusion class I fusion protein, and/or a nucleic acid molecule, and/or a vector, according to the invention. Also provided are pre-fusion class I fusion proteins, nucleic acid molecules, and/or vectors, according to the invention for use in inducing an immune response against said class I fusion protein in a subject. Further provided is the use of the pre-fusion class I fusion protein, and/or nucleic acid molecules, and/or vectors according to the invention for the manufacture of a medicament for use in inducing an immune response against said class I fusion protein in a subject. In certain embodiments, the pre-fusion class I proteins according to the invention are for use as a vaccine.

The pre-fusion class I fusion proteins, nucleic acid molecules and/or vectors according to the invention may be used e.g. in stand-alone treatment and/or prophylaxis of a disease or condition caused by the virus comprising said class I fusion protein, or in combination with other prophylactic and/or therapeutic treatments, such as (existing or future) vaccines, antiviral agents and/or monoclonal antibodies.

The invention further provides methods for preventing and/or treating virus infection in a subject utilizing the pre-fusion class I fusion proteins, nucleic acid molecules and/or vectors according to the invention. In a specific embodiment, a method for preventing and/or treating a virus infection in a subject comprises administering to a subject in need thereof an effective amount of a pre-fusion class I fusion protein, nucleic acid molecule and/or a vector, as described above. A therapeutically effective amount refers to an amount of a class I fusion protein, nucleic acid molecule or vector that is effective for preventing, ameliorating and/or treating a disease or condition resulting from infection by a virus comprising said class I fusion protein. Prevention encompasses inhibiting or reducing the spread of virus or inhibiting or reducing the onset, development or progression of one or more of the symptoms associated with infection by said virus. Amelioration as used in herein may refer to the reduction of visible or perceptible disease symptoms, viremia, or any other measurable manifestation of a viral infection.

For administering to subjects, such as humans, the invention may employ pharmaceutical compositions comprising a pre-fusion class I fusion protein, a nucleic acid molecule and/or a vector as described herein, and a pharmaceutically acceptable carrier or excipient. In the present context, the term "pharmaceutically acceptable" means that the carrier or excipient, at the dosages and concentrations employed, will not cause any unwanted or harmful effects in the subjects to which they are administered. Such pharmaceutically acceptable carriers and excipients are well known in the art (see Remington's Pharmaceutical Sciences, 18th edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]). The pre-fusion class I polypeptides, or nucleic acid molecules, preferably are formulated and administered as a sterile solution although it may also be possible to utilize lyophilized preparations. Sterile solutions are prepared by sterile filtration or by other methods known per se in the art. The solutions are then lyophilized or filled into pharmaceutical dosage containers. The pH of the solution generally is in the range of pH 3.0 to 9.5, e.g. pH 5.0 to 7.5.

In certain embodiments, a composition according to the invention further comprises one or more adjuvants. Adjuvants are known in the art to further increase the immune response to an applied antigenic determinant. The terms "adjuvant" and "immune stimulant" are used interchangeably herein, and are defined as one or more substances that cause stimulation of the immune system. In this context, an adjuvant is used to enhance an immune response to the class I fusion protein of the invention. Examples of suitable adjuvants include aluminium salts such as aluminium hydroxide and/or aluminium phosphate; oil-emulsion compositions (or oil-in-water compositions), including squalene-water emulsions, such as MF59 (see e.g. WO 90/14837); saponin formulations, such as for example QS21 and Immunostimulating Complexes (ISCOMS) (see e.g. U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, and the like; eukaryotic proteins (e.g. antibodies or fragments thereof (e.g. directed against the antigen itself or CD1a, CD3, CD7, CD80) and ligands to receptors (e.g. CD40L, GMCSF, GCSF, etc), which stimulate immune response upon interaction with recipient cells. In certain embodiments the compositions of the invention comprise aluminium as an adjuvant, e.g. in the form of aluminium hydroxide, aluminium phosphate, aluminium potassium phosphate, or combinations thereof, in concentrations of 0.05-5 mg, e.g. from 0.075-1.0 mg, of aluminium content per dose.

In other embodiments, the compositions do not comprise adjuvants.

The invention is further illustrated in the following Examples.

EXAMPLES

Example 1

In order to stabilize the labile pre-fusion conformation of HIV-1 envelope protein, amino acid residues at position 555, 556 and 558 (according to the HXB2 numbering) in the hinge loop were substituted for proline residues. The total gp140 expression, trimeric nature (trimer percentage) and total trimer yield of the envelopes were compared to a variant with the known stabilizing I559P substitution (Sanders et. al., J Virol 2002, supra) and an envelope protein without proline substitutions in the hinge loop. Trimer percentage, yield and stability were determined using ELISA, AlphaLISA and/or SEC-MALS. Part of the wild type hinge loop, the single Pro substitutions, the double Pro substitutions and a triple Pro substitution are shown in Table 3.

Generation of HIV-1 Env Consensus C Sequence

The HIV-1 Env sequence was based on a consensus sequence based on clade C. Therefore an alignment was downloaded (HIV Sequence Alignments. 3,434 sequences in total) from the Los Alamos database (website: www.hiv.lanl.gov/content/index). Only the C-clade ENVs (1,252 sequences) were used in the consensus maker in the Los Alamos HIV database website.

Recombinant proteins based on consensus C with the stabilizing SOS modification (501C-605C) were expressed in Expi293 cells (Life Technologies), as described below. Env proteins used in ELISA contained a C-terminal C-tag and additional 1201C-A433C mutations (Kwon et al. Nat Struct Mol Biol, (2015), 22(7):522-531). Env proteins used in AlphaLISA and SEC-MALS contained a C-terminal SortA-Flag-35GS-His-tag. The cells were transiently transfected using ExpiFectamine293 (Life Technologies) according to the manufacturer's instructions and cultured in a shaking incubator at 37° C. and 8% CO2. The culture supernatants containing HIV envelope protein (Env) were harvested on day 3 (for AlphaLISA) or day 5 (for ELISA and SEC-MALS) after transfection and sterile-filtered. C-tagged Env was purified using C-tag affinity chromatography and the SortA-Flag-35GS-His-tagged Env was purified using *Galanthus nivalus* lectin chromatography, followed by SEC-MALS. The recombinant HIV env proteins were purified by a 2-step purification protocol applying a *Galanthus nivalis*-lectin column (Vectorlabs, AL-1243, lot Z0325) for the initial purification and subsequently a superdex200 Increase column (GE) for the polishing step to remove residual contaminants. For the initial lectin step the culture supernatant was diluted with 40 mM Tris, 500 mM NaCl pH7.5 and passed over a 4 ml CV Tricorn 10-50 Lectin Agarose Column at 4 ml per minute. Subsequently the column was washed with 4 column volumes (CV) of 40 mM Tris, 500 mM NaCl pH7.5 and eluted 4 CV of 40 mM Tris, 500 mM NaCl, 1M Mannopyronoside pH7.5 with an upflow of 1.6 mL/min. The eluate was concentrated using a spin concentrator (50K, Amicon Ultra, Millipore) and the protein was further purified using a superdex200 column using 50 mM Tris, 150 mM NaCl pH 7.4 as running buffer. The second peak contained the HIV gp140 trimer. The fractions containing this peak were again pooled and the protein concentration was determined using OD280 and stored a 4° C. until use. The identity of the band was verified using Western blotting (not shown) SDS-PAGE analysis and Western blot. Cell culture supernatants or purified protein samples were analyzed on 4-12% (w/v) Bis-Tris NuPAGE gels, 1×MOPS (Life Technologies) under reducing or non-reducing conditions and blotted using the iBlot technology (Life Technologies). All procedures were performed according to manufacturer's instructions. For purity analysis the gels were stained with Krypton Infrared Protein Stain (Thermo Scientific) or SYPRO Rubi protein stain (Bio-Rad). The blots were probed with anti-His-HRP. The gels and the blot membranes were scanned on an Odyssey instrument (Li-Cor) and images analyzed using Odyssey 3.0 software (Li-Cor).

Figure 3A:
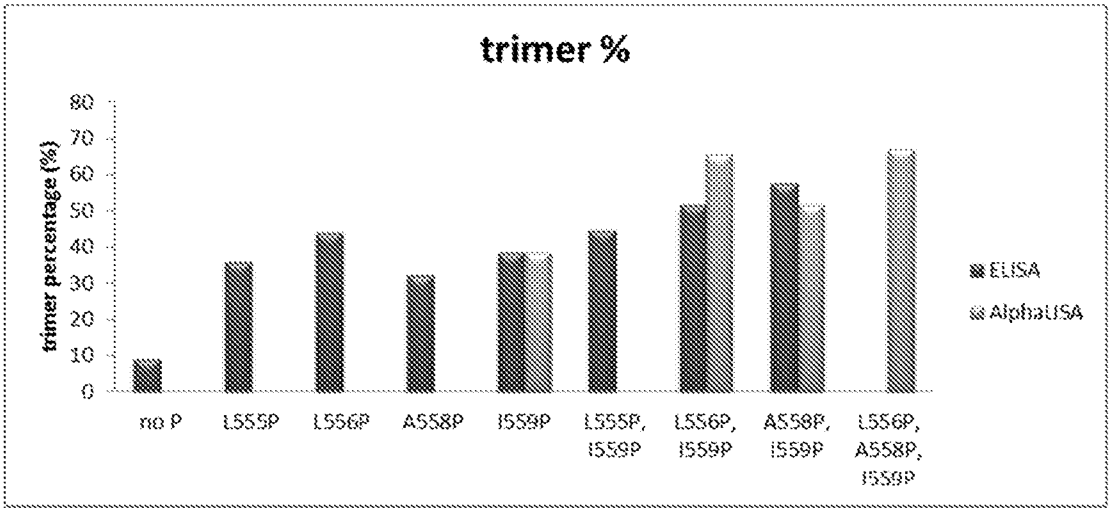
FIG. 3: Trimer percentage and yield of proline substitutions in HIV-1 env sequence based on a consensus of C clade Envs with a stabilizing disulfide at position 501-605 (ConC_SOS). A) Trimer percentage determined using ELISA with C-tag purified Env (black bars) and AlphaLISA on cell-free supernatant (grey bars). The trimer percentage of the I559P variant obtained by ELISA was used to normalize the AlphaLISA dataset. B) Trimer yield determined using ELISA with purified Env (black bars) and AlphaLISA on cell-free supernatant (grey bars). The data was normalized to I559P variant. ND: not determined. Proline substitutions of HIV-1 env variants are described in more detail in Table 3.
Figure 3B:
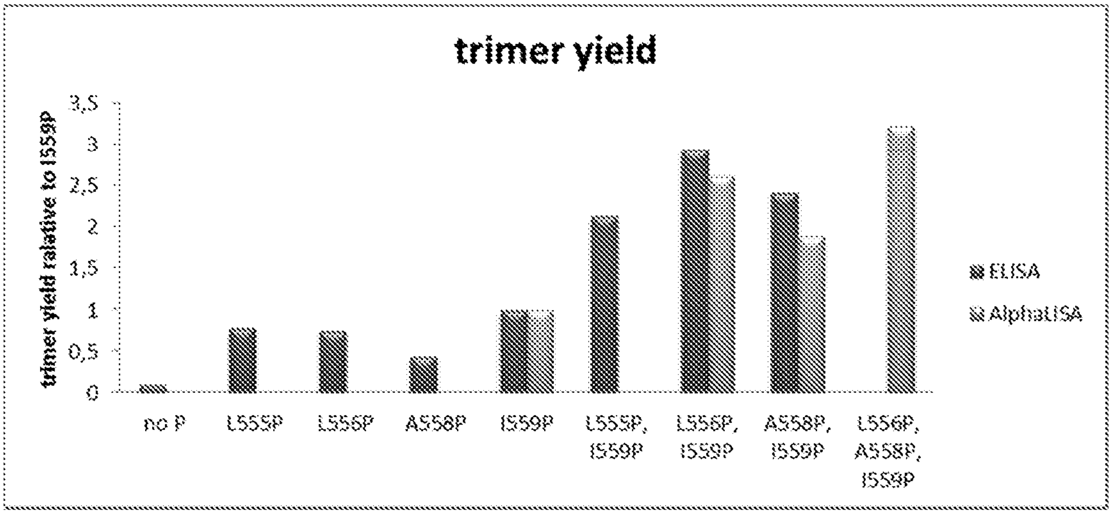

The total Env expression level for input in ELISA was determined by calculation of the area under the curve of the C-tag purification chromatogram. C-tagged Env was captured using His-tagged anti-C-tag VHH. The correct trimeric conformation of the purified protein was confirmed by binding to PGT145 antibody in ELISA. A 100% trimeric Env was taken along as a control to calculate the trimer percentage (FIG. 3A). Trimer yield was calculated by multiplying the trimer percentage with the total Env expression level and normalized to I559P, which was set at 1 (FIG. 3B). All substitutions show higher trimer percentage and yield compared to the protein without proline substitutions in the hinge-loop. All double substitutions increase trimer percentage and in particular trimer yield compared to I559P variant. Based on these finding a triple mutant L556P, A558P, I559P was constructed and compared to I559P and double mutants L556P, I559P and A558P, I559P. These variants were analyzed in cell-free supernatant using AlphaLISA.

AlphaLISA is a bead-based proximity assay in which singlet oxygen molecules, generated by high energy irradiation of Donor beads, transfer to Acceptor beads, which are within a distance of approximately 200 nm. Subsequently, a cascading series of chemical reactions results in a chemiluminescent signal (Eglen et al. Curr Chem Genomics (2008), 1: 2-10). For the AlphaLISA® assay the constructs were equipped with a Flag-His tag (with a 35GS linker in between). The HIV constructs were expressed in Expi293 cells, which were cultured for 3 days in 96 well plates (200 μl/well). Crude supernatants were diluted 120 times in AlphaLISA buffer (PBS+0.05% Tween-20+0.5 mg/mL BSA). Subsequently 10 μl of these dilutions were transferred to a half-area 96-well plate and mixed with 40 μl acceptor beads, mixed with donor beads and PGT145. The sequence of PGT145 was derived from PDB file 3U1S and was expressed like the Envs (no furin added) and purified using MAb select SuRe affinity chromatography. The beads were mixed well before use. After 2 hours of incubation at RT, non-shaking, the signal was measured with Neo (BioTek) The donor beads were conjugated to ProtA (Cat#: AS102M, Lot#1831829, Perkin Elmer), which could bind to the mAb. The acceptor beads were conjugated to an anti-His antibody (Cat#: AL112R, Lot#2036860, Perkin Elmer) to detect the His-tag of the protein. For the quantification of the protein yield, a combination of Nickel-conjugated donor beads (Cat#: AS101M, Lot#: 2027498, Perkin Elmer) together with acceptor beads carrying anti-Flag antibody (Cat#: AL112R, Lot#: 2036860, Perkin Elmer) were used. The average mock signal was subtracted from the AlphaLISA counts measured for the different Env proteins. As a reference the ConC_SOSIP backbone was used, the whole data set was divided by ConC_SOSIP signal, to normalize the signals to the backbone. Trimer percentages were obtained by dividing these normalized signals to the normalized signal obtained for the quantification. The backbone trimer percentage was set to 30% according to the results of SEC-MALS.

Figure 4A:
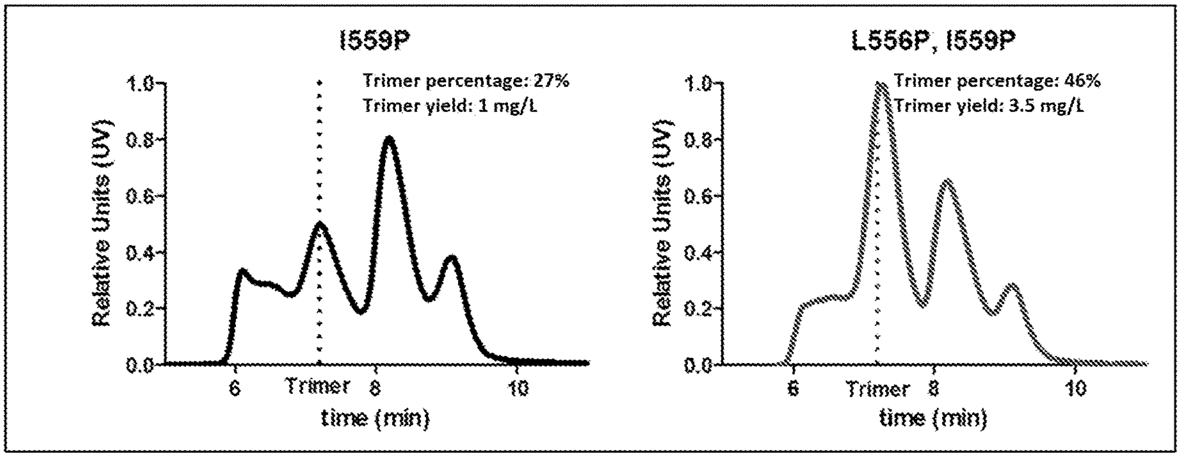
FIG. 4: A) SEC-MALS profile of *Galanthus nivalus* lectin-purified HIV-1 ConC_SOS Env variant with I559P substitution (left) and L556P, I559P double substitution (right). Chromatograms show aggregates (at the left of the chromatogram), followed by trimers, followed by two peaks with smaller subunits. B) Percentage of total trimer population remaining after incubation of crude supernatant of HIV-1 env variants for 1 hour at 60° C., using PGT145 binding in AlphaLISA.

The correct trimeric conformation was confirmed by binding to PGT145 antibody binding and expression levels were quantified by detecting the SortA-Flag-35GS-His-tag. Trimer percentage was calculated by dividing the PGT145 signal by the quantification signal (FIG. 3A). The trimer yield was derived from AlphaLISA by normalizing the PGT145 signal to that of I559P, which was set at 1 (FIG. 3B) The triple mutant has the highest trimer percentage and yield compared to all other variants. Trimer percentage and yield of *Galanthus nivalus* lectin-purified I559P and L556P, I559P were confirmed using size exclusion chromatography (SEC) and multi-angle light scattering (MALS) analysis using a high-performance liquid chromatography system (Agilent Technologies) and miniDAWN TREOS (Wyatt) instrument coupled to a Optilab T-rEX Refractive Index Detector (Wyatt). In total, 40 μg of protein was applied to a TSK-Gel G3000SWx1 column (Tosoh Bioscience) equilibrated in running buffer (150 mM Sodium Phosphate buffer, 50 mM NaCl, pH 7.0) at 1 mL/min. The data were analyzed by the Astra 6 software package and molecular weight calculations were derived from the refractive index signal. The trimer content from SEC-MALS chromatograms were determined by calculating the area under the curve, yielding comparable results as ELISA and AlphaLISA (FIG. 4A). Trimer stability was determined using PGT145 binding in AlphaLISA of crude supernatant that was incubated for 1 hour at 60° C. For the thermostability assay 20 μl crude supernatant was heated at 60° C. for 1 hour, in a PCR block. The plates were centrifuged 5 min. at maximum speed, to remove aggregates. The non-treated and heat treated supernatants were diluted 40×. Then the AlphaLISA assay was performed as described above, using PGT145 as trimer specific antibody and Nickel/Flag for the quantification.

Figure 4B:
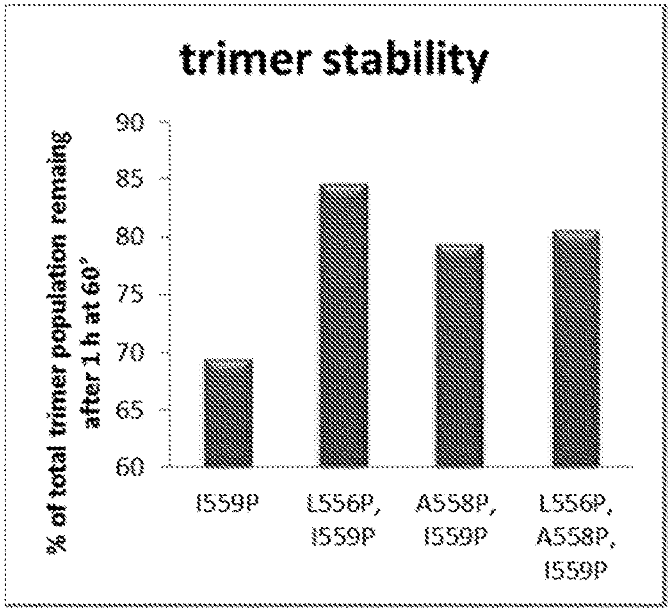

Percentage of total trimer population remaining after incubation was calculated by dividing the PGT145 signal before incubation and the signal after incubation. All double and triple mutants show higher trimer stability than the I559P variant (FIG. 4B). These results show that hinge stabilization is successful for the class I fusion protein of the retrovirus HIV-1.

Example 2

Figure 5A:
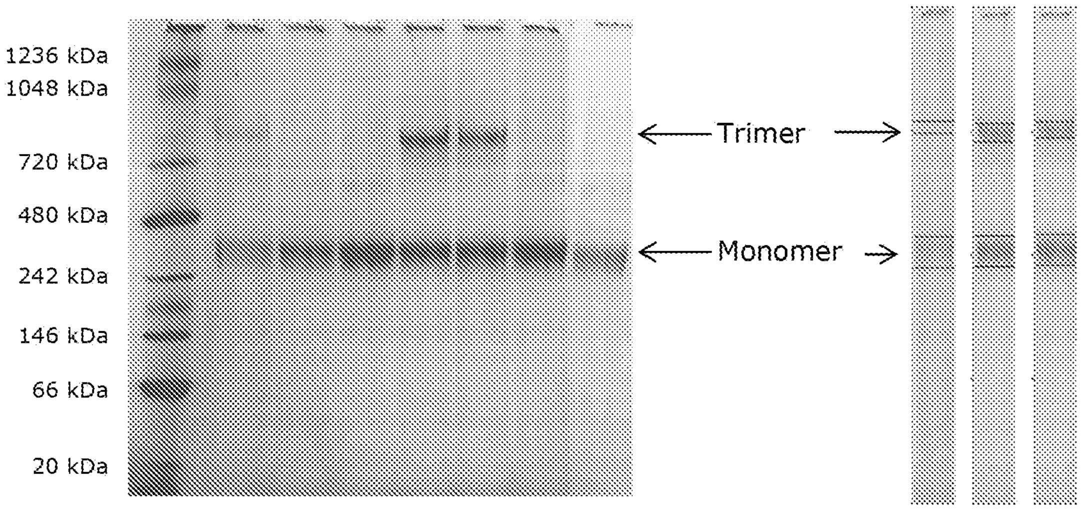
FIG. 5: A) NativePAGE analysis of cell free supernatant of ebola GP variants with proline substitutions in hinge-loop. Supernatants of transfected expi293 cells were analyzed on NativePAGE and stained with Coomassie. Lanes show expression and quaternary structure of variants. B) The trimer and monomer bands of the WT, T577P and L579P mutants were determined and their relative percentages calculated.
Figure 5B:
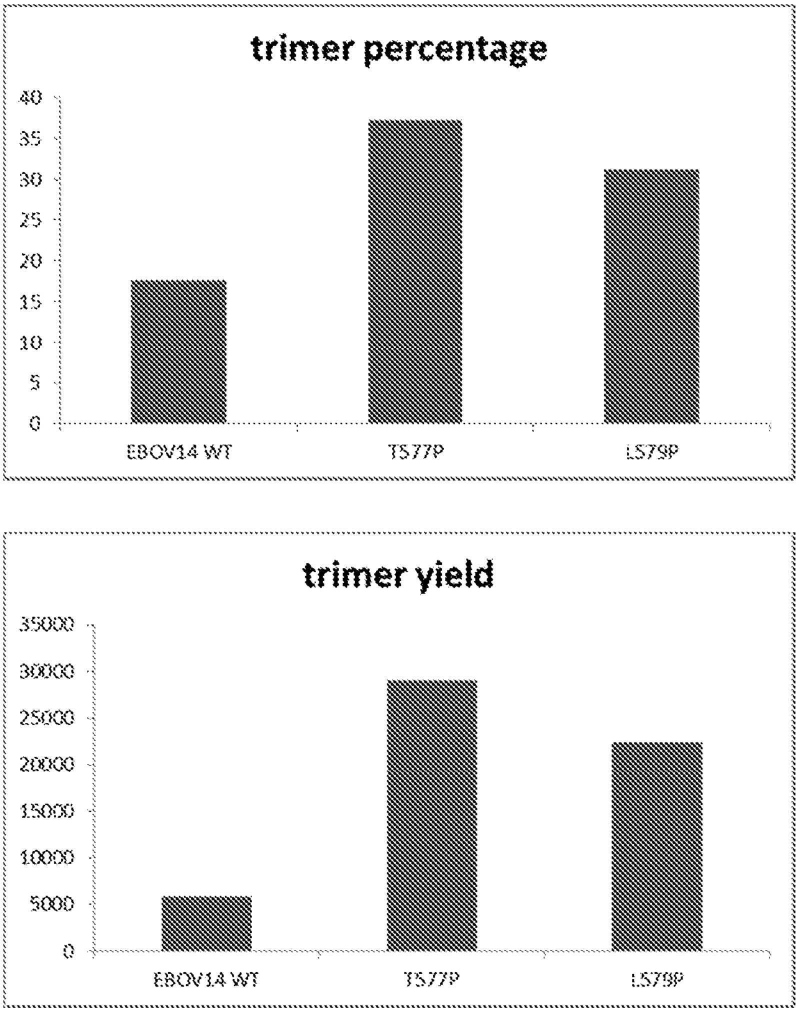

In order to stabilize the pre-fusion conformation of a filovirus fusion protein GP, residues in the hinge loop at position 575, 576, 577, 579, 581 and 583 were substituted to Proline and the expression level, multimeric nature of the Ebola GP and the stability was accessed using NativePAGE and differential scanning fluorometry (DSF), respectively. FIG. 5 shows the NativePAGE analysis of supernatants from ebola GP variants with proline substitutions at position 575, 576, 577, 579, 581 and 583. As shown in FIG. 5 A, only variants with substitutions at positions 577 and 579 showed high expression and had higher trimer content compared to the wt sequence. The trimer and monomer bands of the WT, T577P and L579P mutants were determined (FIG. 5B) and their relative percentages calculated (FIG. 5C). NativePAGE Bis-Tris gels system (Life technologies) was used to analyse the supernatants from transiently transfected cells. Subsequently the gels were stained by Coomassie. The Native PAGE gel was scanned using Biorad ChemiDoc MP. The quantification was done using Biorads Image Lab software, using the "Lane and band" analysis tool. Therefore the protein lanes are highlighted and the protein bands of interest are selected. The software calculates the intensity of the highlighted bands and their relative amounts were calculated.

Next, HIS-tag purified GP variants were tested for temperature stability by DSF. Protein was mixed with SYPRO orange fluorescent dye (Life Technologies 56650) in a 96-well optical qPCR plate. The optimal dye and protein concentration was determined experimentally. All protein dilutions were performed in PBS, and a negative control sample containing the dye only was used as a reference subtraction. The measurement was performed in a qPCR instrument (Applied Biosystems ViiA 7) using the following parameters: a temperature ramp from 25-85° C. with a rate of 0.015° C. per second. Data was collected continuously.

Figure 6:
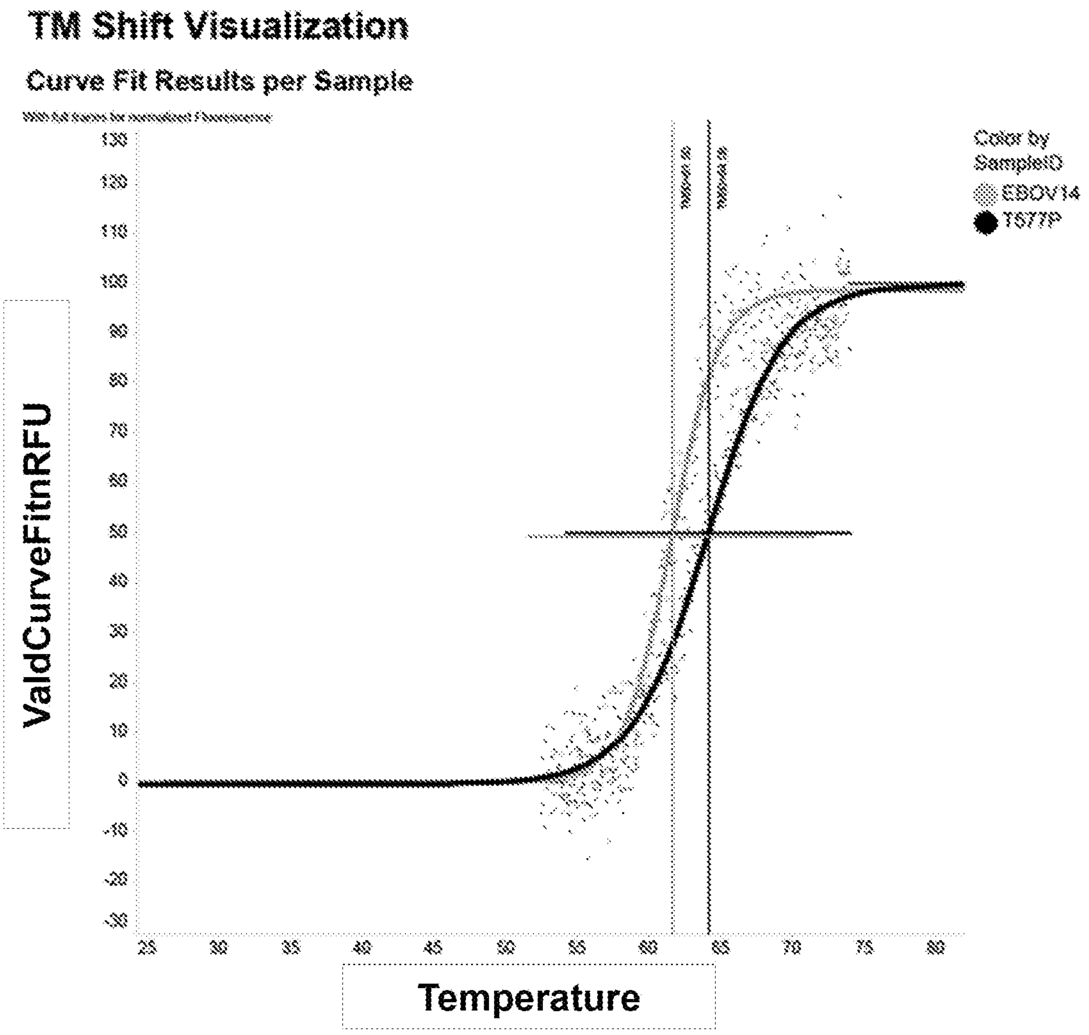
FIG. 6: Analysis of melting temperature (Tm) of wt ebola GP, strain EBOV14 and a variant with the T577P substitution using differential scanning fluorometry (DSF).

The negative first derivative of the Sypro Orange signal measured at several intervals during a temperature ramp up to 85 degrees. Raw data from the Sypro Orange assay was analyzed using an R script which parses ViiA7 output (machine used for the Sypro assay) and merges the sample information with the melt curve data. Spotfire software was used to subtract the controls from the data (buffer with Sypro Orange). Then it determines top and bottom of the melt curves and normalizes the curves for values between 0 and 100. Duplicates are averaged from duplicate runs and Tm determined at half maximal value. Melting temperatures (point where the signal reaches 50% of the maximum value) could be determined after fitting the data using Spotfire for the wt protein (61.5° C.) and the T577P variant (64° C.). The fitted data are shown in FIG. 6. The variant with the T577P substitution showed a higher temperature stability than the wt protein.

To study the universality of the stabilizing effect of T577P, the 577P substitution was also evaluated in the GP of ebola strain Mayinga (NCBI Reference Sequence: NP_066246.1), ebola strain Sudan Gulu (NCBI Reference Sequence: YP_138523.1) As shown in FIG. 7, the proline substitution increased expression levels and trimer content of filovirus GP. These results show that hinge stabilization is also successful for the class I fusion protein of ebola virus.

Example 3

The fusion domain of Influenza is sequestered in the Hemagglutinin protein that has a head domain (mostly HA1) that is responsible for binding to sialic acid (hemagglutination functionality) and a stem domain (mostly HA2) that contains the fusion domain. In order to study the stabilization of the Influenza Hemagglutinin fusion domain, point mutations were made in a so-called mini-HA (#4650) that corresponds to a semi-stable stem region and contains the HA2 ectodomain and a fragment of HA1 (Impagliazzo et. al., Science 24 Aug. 2015). In order to stabilize the semi-stable pre-fusion conformation of Influenza mini-Hemagglutinin 4650, HA2 Ser73 was substituted to Leu or Pro to remove the glycan at position 71 and study the effect of the hydrophobic rigidifying Proline residue versus the hydrophobic Leucine residue in the hinge loop (B-loop). Because the mini-Hemagglutinin did not contain the head domain, a variant was made in which Lys68 was substituted to Gln68 because the Lysine is originally involved in a conserved salt-bridge between the B-loop and the head domain. Because the head was deleted, the salt-bridge was gone and Lysine could be changed to the neutral Glutamine. Recombinant proteins were expressed in 293 Freestyle cells (as described below). Stability of the mini-hemagglutinin variants was accessed by an ELISA in which the multimer content of the protein is measured. Supernatants of transfected cell were tested in multimer ELISA. Plates were coated with the stem-specific broadly neutralizing MAb CR9114 (Dreyfus et. al., Science (2012), 337(6100):1343-8). Supernatants were titrated and incubated with the coated plates. After washing, the captured multimers were incubated with biotinylated CR9114. Next the wells were incubated with HRP-conjugated streptavidin followed by addition of HRP substrate (Impagliazzo et. al., Science 2015). FIG. 8 shows that variants with P73 in the hinge loop (B-loop) showed higher multimer expression than variants with L73. Additionally, a substitution of Tyr to Pro at position 63 of mini-HA #4650 also resulted in an almost 2-fold higher multimer expression (FIG. 8C). These results show that hinge stabilization is also successful for the class I fusion protein of the orthomyxovirus Influenza HA.

Example 4

Expression of Protein Constructs

The constructs were synthesized and codon-optimized at GenScript (Piscataway, N.J. 08854) or at Gene Art (Life Technologies, Carlsbad, Calif.). The constructs were cloned into pCDNA2004 or generated by standard methods involving site-directed mutagenesis and PCR, and sequenced. HEK-Expi293 cells or HEK293F cells were transiently transfected with pCDNA2004 plasmid with the protein insert (and in case of HIV Env 90% env and 10% Furin-pCDNA2004), according to the manufacturer's instructions and cultured for 5 days at 37° C. and 10% CO2. The culture supernatant was harvested and spun for 5 minutes at 300 g to remove cells and cellular debris. The spun supernatant was subsequently sterile filtered using a 0.22 μm vacuum filter and stored at 4° C. until use.

TABLE 1

Standard amino acids, abbreviations and properties

| Amino Acid | 3-Letter | 1-Letter | Side chain polarity | Side chain charge (pH 7.4) |
|---|---|---|---|---|
| alanine | Ala | A | non-polar | Neutral |
| arginine | Arg | R | polar | Positive |
| asparagine | Asn | N | polar | Neutral |
| aspartic acid | Asp | D | polar | Negative |
| cysteine | Cys | C | non-polar | Neutral |
| glutamic acid | Glu | E | polar | Negative |
| glutamine | Gln | Q | polar | Neutral |
| glycine | Gly | G | non-polar | Neutral |
| histidine | His | H | polar | positive (10%) neutral (90%) |
| isoleucine | Ile | I | non-polar | Neutral |
| leucine | Leu | L | non-polar | Neutral |
| lysine | Lys | K | polar | Positive |
| methionine | Met | M | non-polar | Neutral |
| phenylalanine | Phe | F | non-polar | Neutral |
| proline | Pro | P | non-polar | Neutral |
| serine | Ser | S | polar | Neutral |
| threonine | Thr | T | polar | Neutral |
| tryptophan | Trp | W | non-polar | Neutral |
| tyrosine | Tyr | Y | polar | Neutral |
| valine | Val | V | non-polar | Neutral |

TABLE 2

| | | |
|---|---|---|
| HIV-1, HXB2 | 540 QARQLLSGIVQQQNNLLRAIEAQQHLLQLTVWGIKQLQARI | 580 (SEQ ID NO: 1) |
| HIV-1, ConC | 539 QARQLLSGIVQQQSNLLRAIEAQQHMLQLTVWGIKQLQTRV | 579 (SEQ ID NO: 2) |
| HIV-2, BAH97710.1 | 538 QSRTLLAGIVQQQQQLLDAVKRQQELLRLTVWGTKNLQSRV | 578 (SEQ ID NO: 30) |

TABLE 2-continued

| Filo: alpha 1-hingeloop-alpha2 | | | |
|---|---|---|---|
| Ebola, mayinga | 553 | GLICGLRQLANETTQALQLFLRATTELRTFSILNRKAIDFLLQR | 596 (SEQ ID NO: 10) |
| Marburg | 554 | NLVCRLRRLANQTAKSLELLLRVTTEERTFSLINRHAIDFLLAR | 597 (SEQ ID NO: 14) |
| Influenza A, H1 | 38 | QKSTQNAINGITNKVNSVIEKMNTQFTAVGKEFNKLERRMENLNKKVDDGFID | (SEQ ID NO: 18) |
| Influenza A, H3 | 47 | LKSTQAAINQINGKLNRLIGKTNEKFHQIEKEFSEVEGRIQDLEKYVEDTKID | (SEQ ID NO: 22) |
| Influenza B, B/Yamanashi/166/1998 | 38 | LKSTQEAINKITKNLNS-LELEVKNLQRLSGAMDELHNEILELDEKVDDLRAD | (SEQ ID NO: 26) |

TABLE 3

Hinge loop of HIV-1 ConcC, residues 547-571 (with Env numbering following standard HXB2 convention) and variants with Proline substitutions

| Code | substitution | sequence |
|---|---|---|
| HIV150400: | ConC_SOS | LLSGIVQQQSNLLRAIEAQQHMLQLTVWG |
| HIV150399: | $I_{559}P$ | LLSGIVQQQSNLLRA**P**EAQQHMLQLTVWG |
| HIV150401: | $A_{558}P$ | LLSGIVQQQSNLLR**PI**EAQQHMLQLTVWG |
| HIV150402: | $L_{556}P$ | LLSGIVQQQSNL**P**RA**I**EAQQHMLQLTVWG |

TABLE 3-continued

Hinge loop of HIV-1 ConcC, residues 547-571 (with Env numbering following standard HXB2 convention) and variants with Proline substitutions

| Code | substitution | sequence |
|---|---|---|
| HIV150403: | $L_{555}P$ | LLSGIVQQQSNPLRA**I**EAQQHMLQLTVWG |
| HIV150404: | $_{558}P_{559}P$ | LLSGIVQQQSNLLR**PP**EAQQHMLQLTVWG |
| HIV150405: | $_{559}P_{559}P$ | LLSGIVQQQSNL**P**RA**P**EAQQHMLQLTVWG |
| HIV160114: | $_{556}P_{558}P_{559}P$ | LLSGIVQQQSNL**P**R**PP**EAQQHMLQLTVWG |

Sequences

HIV-1 HXB2 gp160 with signal peptide.

(SEQ ID NO: 9)

MRVKEKYQHLWRWGWRWGTMLLGMLMICSATEKLWVTVYYGVPVWKEATTTLFCASDAKAYDTEVHNV

WATHACVPTDPNPQEVVLVNVTENFNMWKNDMVEQMHEDIISLWDQSLKPCVKLTPLCVSLKCTDLKN

DTNTNSSSGRMIMEKGEIKNCSFNISTSIRGKVQKEYAFFYKLDIIPIDNDTTSYKLTSCNTSVITQA

CPKVSFEPIPIHYCAPAGFAILKCNNKTFNGTGPCTNVSTVQCTHGIRPVVSTQLLLNGSLAEEEVVI

RSVNFTDNAKTIIVQLNTSVEINCTRPNNNTRKRIRIQRGPGRAFVTIGKIGNMRQAHCNISRAKWNN

TLKQIASKLREQFGNNKTIIFKQSSGGDPEIVTHSFNCGGEFFYCNSTQLFNSTWFNSTWSTEGSNNT

EGSDTITLPCRIKQIINMWQKVGKAMYAPPISGQIRCSSNITGLLLTRDGGNSNNESEIFRPGGGDMR

DNWRSELYKYKVVKIEPLGVAPTKAKRRVVQREKRAVGIGALFLGFLGAAGSTMGAASMTLTVQARQL

LSGIVQQQNNLLRAIEAQQHLLQLTVWGIKQLQARILAVERYLKDQQLLGIWGCSGKLICTTAVPWNA

SWSNKSLEQIWNHTTWMEWDREINNYTSLIHSLIEESQNQQEKNEQELLELDKWASLWNWFNITNWLW

YIKLFIMIVGGLVGLRIVFAVLSIVNRVRQGYSPLSFQTHLPTPRGPDRPEGIEEEGGERDRDRSIRL

VNGSLALIWDDLRSLCLFSYHRLRDLLLIVTRIVELLGRRGWEALKYWWNLLQYWSQELKNSAVSLLN

ATAIAVAEGTDRVIEVVQGACRAIRHIPRRIRQGLERILL

HIV-2 Envelope protein.

(SEQ ID NO: 35)

MAHINSHLLISLLLISVYGCMCKQYVTVFYGIPAWRNATVPLFCATANRDTWGTVQCLPD

SGDYTEISVNITEAFDAWNNTVTEQAVDDVWNLFETSLKPCVKLTPLCVAMNCSTNNTRT

NNTTASTTTGNSTTPIVVNEAIPCVKANNCSGIGLEDVVNCTFNMTGLRQDERKQYNDTW

YRRDLECEGTRCYMRTCNTSVIQESCDKHYWDSLRFRYCAPPGYAILRCNDTNYSGFMHN

-continued

CSKVVVSSCTRMMETQTSTWFGFNGTRAENRTYMYWHGRDNRTIISLNRYYNLTMHCRRP

GNKTVLPITIMSGRRFHSRPVINERPRQAWCWFEGNWTEAMREVKETVMKHPRYTGIKNI

TKINLVGPSAGSDPEARYMWTNCRGEFFYCNMTWFLNWVEGKNGTKRNYVPCHIRQIVNT

WHKVGKYVYLPPREGLLSCNSTVTSIIANIEWIDSNETNITMSAEVGELYRLELGDYKLV

EITPIGFAPTNIKRYSSATPRNRRGVMVLGELGFLATAGSAMGAASLTLSAQSRTLLAGI

VQQQQQLLDAVKRQQELLRLTVWGTKNLQSRVTAIEKYLKDQALLNSWGCAFRQVCHTTV

PWPNESLTPNWTDMTWQQWEEKVHYLDANITQLLEEAQIQQEKNMYELQKLNHWDVFSNW

FDFTSWMAYIRLGLYVVVGLIVLRIVIYVIQMLARLRKGYRPVFSSPPSYTQQIPIHKHR

GQPANEETEDEGGREGDYRSWPWQIEYAHFLIRQLRNLLIWLYNGCRNLLLRTSQILQPA

LQPLRLSLAYLQYGISWLQEAIQAATRAAGETLANAGRALWEALRRTAGAIIAVPRRIRQ

GLELALL

EBOLA GP (STRAIN MAYINGA-76)

(SEQ ID NO: 13)

MGVTGILQLPRDRFKRTSFFLWVIILFQRTFSIPLGVIHNSTLQVSDVDKLVCRDKLSSTNQLRSVGL

NLEGNGVATDVPSATKRWGFRSGVPPKVVNYEAGEWAENCYNLEIKKPDGSECLPAAPDGIRGFPRCR

YVHKVSGTGPCAGDFAFHKEGAFFLYDRLASTVIYRGTTFAEGVVAFLILPQAKKDFFSSHPLREPVN

ATEDPSSGYYSTTIRYQATGFGTNETEYLFEVDNLTYVQLESRFTPQFLLQLNETIYTSGKRSNTTGK

LIWKVNPEIDTTIGEWAFWETKKNLTRKIRSEELSFTVVSNGAKNISGQSPARTSSDPGTNTTTEDHK

IMASENSSAMVQVHSQGREAAVSHLTTLATISTSPQSLTTKPGPDNSTHNTPVYKLDISEATQVEQHH

RRTDNDSTASDTPSATTAAGPPKAENTNTSKSTDFLDPATTTSPQNHSETAGNNNTHHQDTGEESASS

GKLGLITNTIAGVAGLITGGRRTRREAIVNAQPKCNPNLHYWTTQDEGAAIGLAWIPYFGPAAEGIYI

EGLMHNQDGLICGLRQLANETTQALQLFLRATTELRTFSILNRKAIDFLLQRWGGTCHILGPDCCIEP

HDWTKNITDKIDQIIHDFVDKTLPDQGDNDNWWTGWRQWIPAGIGVTGVIIAVIALFCICKFVF

MARBURG GP (SEQ ID NO: 17)

MKTTCLLISLILIQGVKTLPILEIASNIQPQNVDSVCSGTLQKTEDVHLMGFTLSGQKVADSPLEASK

RWAFRAGVPPKNVEYTEGEEAKTCYNISVTDPSGKSLLLDPPTNIRDYPKCKTIHHIQGQNPHAQGIA

LHLWGAFFLYDRIASTTMYRGKVFTEGNIAAMIVNKTVHKMIFSRQGQGYRHMNLTSTNKYWTSSNGT

QTNDTGCFGTLQEYNSTKNQTCAPSKKPLPLPTAHPEVKLTSTSTDATKLNTTDPNSDDEDLTTSGSG

SGEQEPYTTSDAATKQGLSSTMPPTPSPQPSTPQQGGNNTNHSQGVVTEPGKTNTTAQPSMPPHNTTT

ISTNNTSKHNLSTPSVPIQNATNYNTQSTAPENEQTSAPSKTTLLPTENPTTAKSTNSTKSPTTTVPN

TTNKYSTSPSPTPNSTAQHLVYFRRKRNILWREGDMFPFLDGLINAPIDFDPVPNTKTIFDESSSSGA

SAEEDQHASPNISLTLSYFPKVNENTAHSGENENDCDAELRIWSVQEDDLAAGLSWIPFFGPGIEGLY

TAGLIKNQNNLVCRLRRLANQTAKSLELLLRVTTEERTFSLINRHAIDFLLARWGGTCKVLGPDCCIG

IEDLSRNISEQIDQIKKDEQKEGTGWGLGGKWWTSDWGVLTNLGILLLLSIAVLIALSCICRIFTKYI

G

Hemagglutinin Influenza A virus (group 1)(A/Brisbane/59/2007(H1N1).

(SEQ ID NO: 21)

MKVKLLVLLCTFTATYADTICIGYHANNSTDTVDTVLEKNVTVTHSVNLLENSHNGKLCL

LKGIAPLQLGNCSVAGWILGNPECELLISKESWSYIVEKPNPENGTCYPGHFADYEELRE

QLSSVSSFERFEIFPKESSWPNHTVTGVSASCSHNGESSFYRNLLWLTGKNGLYPNLSKS

YANNKEKEVLVLWGVHHPPNIGNQKALYHTENAYVSVVSSHYSRKFTPEIAKRPKVRDQE

GRINYYWTLLEPGDTIIFEANGNLIAPRYAFALSRGFGSGIINSNAPMDKCDAKCQTPQG

AINSSLPFQNVHPVTIGECPKYVRSAKLRMVTGLRNIPSIQSRGLFGAIAGFIEGGWTGM

-continued

VDGWYGYHHQNEQGSGYAADQKSTQNAINGITNKVNSVIEKMNTQFTAVGKEFNKLERRM

ENLNKKVDDGFIDIWTYNAELLVLLENERTLDFHDSNVKNLYEKVKSQLKNNAKEIGNGC

FEFYHKCNDECMESVKNGTYDYPKYSEESKLNREKIDGVKLESMGVYQILAIYSTVASSL

VLLVSLGAISFWMCSNGSLQCRICI

Hemagglutinin Influenza A virus (group 2)K7N5L2_9INFA.
(SEQ ID NO: 25)

QKLPGNDNST ATLCLGHHAV PNGTIVKTIT NDQIEVTNAT ELVQSSSTGG

ICDSPHQILD GENCTLIDAL LGDPQCDGFQ NKKWDLFVER SKAYSNCYPY

DVPDYASLRS LVASSGTLEF NNESFNWTGV TQNGTSSACK RRSNNSFFSR

LNWLTHLKFK YPALNVTMPN NEKFDKLYIW GVHHPGTDND QISLYAQASG

RITVSTKRSQ QTVIPNIGSR PRVRDIPSRI SIYWTIVKPG DILLINSTGN

LIAPRGYFKI RSGKSSIMRS DAPIGKCNSE CITPNGSIPN DKPFQNVNRI

TYGACPRYVK QNTLKLATGM RNVPEKQTQG IFGAIAGFIE NGWEGMVDGW

YGFRHQNSEG IGQAADLKST QAAINQINGK LNRLIGKTNE KFHQIEKEFS

EVEGRIQDLE KYVEDTKIDL WSYNAELLVA LENQHTIDLT DSEMNKLFER

TKKQLRENAE DMGNGCFKIY HKCDNACIGS IRNGTYDHDV YRDEALNNRF

QIK

Hemagglutinin Influenza B virus (B/Yamanashi/166/1998)
(SEQ ID NO: 29)

MKAIIVLLMVVTSNADRICTGITSSNSPHVVKTATQGEVNVTGVIPLTTTPTKSHFANLK

GTKTRGKLCPTCLNCTDLDVALGRPMCVGVTPSAKASILHEVRPVTSGCFPIMHDRTKIR

QLPNLLRGYEKIRLSTQNVINAEKAPGGPYRLGTSGSCPNATSRSGFFATMAWAVPKDNN

KTATNPLTVEVPHICTKEEDQITVWGFHSDDKTQMKNLYGDSNPQKFTSSANGVTTHYVS

QIGGFPDQTEDGGLPQSGRIVVDYMVQKPGKTGTIVYQRGILLPQKVWCASGRSKVIKGS

LPLIGEADCLHEKYGGLNKSKPYYTGEHAKAIGNCPIWVKTPLKLANGTKYRPPAKLLKE

RGFFGAIAGFLEGGWEGMIAGWHGYTSHGAHGVAVAADLKSTQEAINKITKNLNSLSELE

VKNLQRLSGAMDELHNEILELDEKVDDLRADTISSQIELAVLLSNEGIINSEDEHLLALE

RKLKKMLGPSAVDIGNGCFETKHKCNQTCLDRIAAGTFNAGEFSLPTFDSLNITAASLND

DGLDNHTILLYYSTAASSLAVTLMIAIFIVYMISRDNVSCSICL

The invention claimed is:

1. A stable pre-fusion class I fusion protein, comprising one or more mutations in the hinge-loop that is present between the base helix and the RR1, wherein the one or more mutations comprise a mutation of one or more hydrophobic amino acid residues into Pro, and wherein the class I fusion protein is a filovirus fusion F protein, a retroviral envelope protein, or an influenza hemagglutinin (HA) protein.

2. The fusion protein according to claim 1, wherein the class I fusion protein is an Ebola virus F protein.

3. The fusion protein according to claim 2, comprising a mutation in the hinge loop of the amino acid residue Thr at position 577 and/or a mutation of the amino acid residue Leu at position 579.

4. The fusion protein according to claim 1, wherein the class I fusion protein is an Ebola virus F protein comprising an amino acid sequence selected from the group consisting of:

(SEQ ID NO: 11)
GLICGLRQLANETTQALQLFLRATPELRTFSILNRKAIDFLLQR;
and (SEQ ID NO: 12)
GLICGLRQLANETTQALQLFLRATTEPRTFSILNRKAIDFLLQR.

5. The fusion protein according to claim 1, wherein the class I fusion protein is a Marburg virus F protein.

6. The fusion protein according to claim 5, comprising a mutation in the hinge loop of the amino acid residue Thr at position 578, and/or a mutation of the amino acid residue Glu at position 580.

7. The fusion protein according to claim 5, wherein the class I fusion protein is a Marburg virus F protein comprising an amino acid sequence selected from the group consisting of:

(SEQ ID NO: 15)
NLVCRLRRLANQTAKSLELLLRVTPEERTFSLINRHAIDFLLAR;
and (SEQ ID NO: 16)
NLVCRLRRLANQTAKSLELLLRVTTEPRTFSLINRHAIDFLLAR.

8. The fusion protein according to claim 1, wherein the class I fusion protein is a retroviral HIV-1 envelope protein.

9. The fusion protein according to claim 8, comprising a mutation in the hinge loop of the amino acid residue Leu at position 555, a mutation of amino acid residue Leu at position 556, and/or a mutation of the amino acid residue Ala at position 558.

10. The fusion protein according to claim 8, wherein the class I fusion protein is a HIV-1 envelope protein comprising an amino acid sequence selected from the group consisting of:

(SEQ ID NO: 3)
QARQLLSGIVQQQNNPLRAIEAQQHLLQLTVWGIKQLQARI;

(SEQ ID NO: 4)
QARQLLSGIVQQQNNLPRAIEAQQHLLQLTVWGIKQLQARI;

(SEQ ID NO: 5)
QARQLLSGIVQQQNNLLRPIEAQQEILLQLTVWGIKQLQARI;

(SEQ ID NO: 6)
QARQLLSGIVQQQSNPLRAIEAQQHMLQLTVWGIKQLQTRV;

(SEQ ID NO: 7)
QARQLLSGIVQQQSNLPRAIEAQQHMLQLTVWGIKQLQTRV;
and (SEQ ID NO: 8)
QARQLLSGIVQQQSNLLRPIEAQQHMLQLTVWGIKQLQTRV.

11. The fusion protein according to claim 1, wherein the class I fusion protein is a retroviral HIV-2 envelope protein.

12. The fusion protein according to claim 11, comprising a mutation in the hinge loop of the amino acid residue Leu at position 553 and/or a mutation of amino acid residue Leu at position 554, a mutation of amino acid residue Ala at position 556, and/or a mutation of amino acid residue Val at position 557.

13. The fusion protein according to claim 11, wherein the class I fusion protein is a HIV-2 envelope protein comprising an amino acid sequence selected from the group consisting of:

(SEQ ID NO: 31)
LLAGIVQQQQQPLDAVKRQQELLRLTVWG;

(SEQ ID NO: 32)
LLAGIVQQQQQLPDAVKRQQELLRLTVWG;

(SEQ ID NO: 33)
LLAGIVQQQQQLLDPVKRQQELLRLTVWG;
and (SEQ ID NO: 34)
LLAGIVQQQQQLLDAPKRQQELLRLTVWG.

14. The fusion protein according to claim 1, wherein the class I fusion protein is an influenza H1 hemagglutinin (HA) protein.

15. The fusion protein according to claim 14, comprising a mutation in the hinge loop (B-loop) of HA2 of the amino acid residue Phe at position 63 and/or a mutation of the amino acid residue Leu at position 73.

16. The fusion protein according to claim 14, wherein the class I fusion protein is an influenza H1 hemagglutinin (HA) protein comprising an amino acid sequence selected from the group consisting of:

(SEQ ID NO: 19)
QKSTQNAINGITNKVNSVIEKMNTQPTAVGKEFNKLERRMENLNKKVDDG
FID;
and (SEQ ID NO: 20)
QKSTQNAINGITNKVNSVIEKMNTQFTAVGKEFNKPERRMENLNKKVDDG
FID.

17. The fusion protein according to claim 1, wherein the class I fusion protein is an influenza H3 hemagglutinin (HA) protein.

18. The fusion protein according to claim 17, comprising a mutation in the hinge loop (B-loop) of HA2 of the amino acid residue Phe at position 72 and/or a mutation of the amino acid residue Val at position 82.

19. The fusion protein according to claim 17, wherein the class I fusion protein is an influenza H3 hemagglutinin (HA) protein comprising an amino acid sequence selected from the group consisting of:

(SEQ ID NO: 23)
LKSTQAAINQINGKLNRLIGKTNEKPHQIEKEFSEVEGRIQDLEKYVEDT
KID;
and (SEQ ID NO: 24)
LKSTQAAINQINGKLNRLIGKTNEKFHQIEKEFSEPEGRIQDLEKYVEDT
KID.

20. The fusion protein according to claim 1, wherein the class I fusion protein is an influenza hemagglutinin (HA) polypeptide of an influenza B virus.

21. The fusion protein according to claim 20, comprising a mutation in the hinge loop (B-loop) of HA2 of the amino acid residue Leu at position 62 and/or a mutation of the amino acid Leu at position 72.

22. The fusion protein according to claim 20, wherein the class I fusion protein is an influenza hemagglutinin (HA) polypeptide of an influenza B virus comprising an amino acid sequence selected from the group consisting of:

```
                                          (SEQ ID NO: 27)
LKSTQEAINKITKNLNSLELEVKNPQRLSGAMDELHNEILELDEKVDDL

RAD;
and
                                          (SEQ ID NO: 28)
LKSTQEAINKITKNLNSLELEVKNLQRLSGAMDEPHNEILELDEKVDDL

RAD.
```

23. A nucleic acid sequence encoding a protein according to claim 1.

24. A composition comprising a protein and/or a nucleic acid according to claim 1.

25. A composition comprising a nucleic acid according to claim 23.

* * * * *

SEQUENCE LISTING

<160> NUMBER OF SEQ ID NOS: 35

<210> SEQ ID NO 1
<211> LENGTH: 41
<212> TYPE: PRT
<213> ORGANISM: Artificial Sequence
<220> FEATURE:
<223> OTHER INFORMATION: hinge loop HIV-1 env

<400> SEQUENCE: 1

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Ile
        35                  40

-continued

<210> SEQ ID NO 2
<211> LENGTH: 41
<212> TYPE: PRT
<213> ORGANISM: Artificial Sequence
<220> FEATURE:
<223> OTHER INFORMATION: hinge loop HIV-1 env

<400> SEQUENCE: 2

```
Gln Ala Arg Gln Leu Leu Ser Gly Ile Val Gln Gln Gln Ser Asn Leu
1               5                   10                  15

Leu Arg Ala Ile Glu Ala Gln Gln His Met Leu Gln Leu Thr Val Trp
            20                  25                  30

Gly Ile Lys Gln Leu Gln Thr Arg Val
        35                  40
```

<210> SEQ ID NO 3
<211> LENGTH: 41
<212> TYPE: PRT
<213> ORGANISM: Artificial Sequence
<220> FEATURE:
<223> OTHER INFORMATION: mutated hinge loop HIV-1 env

<400> SEQUENCE: 3

```
Gln Ala Arg Gln Leu Leu Ser Gly Ile Val Gln Gln Gln Asn Asn Pro
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Ile
        35                  40
```

<210> SEQ ID NO 4
<211> LENGTH: 41
<212> TYPE: PRT
<213> ORGANISM: Artificial Sequence
<220> FEATURE:
<223> OTHER INFORMATION: mutated hinge loop HIV-1 env

<400> SEQUENCE: 4

```
Gln Ala Arg Gln Leu Leu Ser Gly Ile Val Gln Gln Gln Asn Asn Leu
1               5                   10                  15

Pro Arg Ala Ile Glu Ala Gln Gln His Leu Leu Gln Leu Thr Val Trp
            20                  25                  30

Gly Ile Lys Gln Leu Gln Ala Arg Ile
        35                  40
```

<210> SEQ ID NO 5
<211> LENGTH: 41
<212> TYPE: PRT
<213> ORGANISM: Artificial Sequence
<220> FEATURE:
<223> OTHER INFORMATION: mutated hinge loop HIV-1 env

<400> SEQUENCE: 5

```
Gln Ala Arg Gln Leu Leu Ser Gly Ile Val Gln Gln Gln Asn Asn Leu
1               5                   10                  15

Leu Arg Pro Ile Glu Ala Gln Gln His Leu Leu Gln Leu Thr Val Trp
            20                  25                  30

Gly Ile Lys Gln Leu Gln Ala Arg Ile
        35                  40
```

<210> SEQ ID NO 6
<211> LENGTH: 41

-continued

<212> TYPE: PRT
<213> ORGANISM: Artificial Sequence
<220> FEATURE:
<223> OTHER INFORMATION: mutated hinge loop HIV-1 env

<400> SEQUENCE: 6

Gln Ala Arg Gln Leu Leu Ser Gly Ile Val Gln Gln Gln Ser Asn Pro
1 5 10 15

Leu Arg Ala Ile Glu Ala Gln Gln His Met Leu Gln Leu Thr Val Trp
20 25 30

Gly Ile Lys Gln Leu Gln Thr Arg Val
35 40

<210> SEQ ID NO 7
<211> LENGTH: 41
<212> TYPE: PRT
<213> ORGANISM: Artificial Sequence
<220> FEATURE:
<223> OTHER INFORMATION: mutated hinge loop HIV-1 env

<400> SEQUENCE: 7

Gln Ala Arg Gln Leu Leu Ser Gly Ile Val Gln Gln Gln Ser Asn Leu
1 5 10 15

Pro Arg Ala Ile Glu Ala Gln Gln His Met Leu Gln Leu Thr Val Trp
20 25 30

Gly Ile Lys Gln Leu Gln Thr Arg Val
35 40

<210> SEQ ID NO 8
<211> LENGTH: 41
<212> TYPE: PRT
<213> ORGANISM: Artificial Sequence
<220> FEATURE:
<223> OTHER INFORMATION: mutated hinge loop HIV-1 env

<400> SEQUENCE: 8

Gln Ala Arg Gln Leu Leu Ser Gly Ile Val Gln Gln Gln Ser Asn Leu
1 5 10 15

Leu Arg Pro Ile Glu Ala Gln Gln His Met Leu Gln Leu Thr Val Trp
20 25 30

Gly Ile Lys Gln Leu Gln Thr Arg Val
35 40

<210> SEQ ID NO 9
<211> LENGTH: 856
<212> TYPE: PRT
<213> ORGANISM: Artificial Sequence
<220> FEATURE:
<223> OTHER INFORMATION: HIV-1 HXB2 gp160 with signal peptide

<400> SEQUENCE: 9

Met Arg Val Lys Glu Lys Tyr Gln His Leu Trp Arg Trp Gly Trp Arg
1 5 10 15

Trp Gly Thr Met Leu Leu Gly Met Leu Met Ile Cys Ser Ala Thr Glu
20 25 30

Lys Leu Trp Val Thr Val Tyr Tyr Gly Val Pro Val Trp Lys Glu Ala
35 40 45

Thr Thr Thr Leu Phe Cys Ala Ser Asp Ala Lys Ala Tyr Asp Thr Glu
50 55 60

Val His Asn Val Trp Ala Thr His Ala Cys Val Pro Thr Asp Pro Asn
65 70 75 80

-continued

```
Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
        435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg Ala
```

-continued

```
            500                 505                 510

Val Gly Ile Gly Ala Leu Phe Leu Gly Phe Leu Gly Ala Ala Gly Ser
        515                 520                 525

Thr Met Gly Ala Ala Ser Met Thr Leu Thr Val Gln Ala Arg Gln Leu
    530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
                565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
        595                 600                 605

Pro Trp Asn Ala Ser Trp Ser Asn Lys Ser Leu Glu Gln Ile Trp Asn
    610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
                645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
        675                 680                 685

Val Gly Gly Leu Val Gly Leu Arg Ile Val Phe Ala Val Leu Ser Ile
    690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
                725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
        755                 760                 765

His Arg Leu Arg Asp Leu Leu Leu Ile Val Thr Arg Ile Val Glu Leu
    770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
                805                 810                 815

Ala Thr Ala Ile Ala Val Ala Glu Gly Thr Asp Arg Val Ile Glu Val
            820                 825                 830

Val Gln Gly Ala Cys Arg Ala Ile Arg His Ile Pro Arg Arg Ile Arg
        835                 840                 845

Gln Gly Leu Glu Arg Ile Leu Leu
    850                 855


<210> SEQ ID NO 10
<211> LENGTH: 44
<212> TYPE: PRT
<213> ORGANISM: Artificial Sequence
<220> FEATURE:
<223> OTHER INFORMATION: hinge loop Ebola virus GP

<400> SEQUENCE: 10

Gly Leu Ile Cys Gly Leu Arg Gln Leu Ala Asn Glu Thr Thr Gln Ala
```

```
1               5                   10                  15

Leu Gln Leu Phe Leu Arg Ala Thr Thr Glu Leu Arg Thr Phe Ser Ile
            20                  25                  30

Leu Asn Arg Lys Ala Ile Asp Phe Leu Leu Gln Arg
        35                  40


<210> SEQ ID NO 11
<211> LENGTH: 44
<212> TYPE: PRT
<213> ORGANISM: Artificial Sequence
<220> FEATURE:
<223> OTHER INFORMATION: mutated hinge loop Ebola GP

<400> SEQUENCE: 11

Gly Leu Ile Cys Gly Leu Arg Gln Leu Ala Asn Glu Thr Thr Gln Ala
1               5                   10                  15

Leu Gln Leu Phe Leu Arg Ala Thr Pro Glu Leu Arg Thr Phe Ser Ile
            20                  25                  30

Leu Asn Arg Lys Ala Ile Asp Phe Leu Leu Gln Arg
        35                  40


<210> SEQ ID NO 12
<211> LENGTH: 44
<212> TYPE: PRT
<213> ORGANISM: Artificial Sequence
<220> FEATURE:
<223> OTHER INFORMATION: mutated hinge loop Ebola GP

<400> SEQUENCE: 12

Gly Leu Ile Cys Gly Leu Arg Gln Leu Ala Asn Glu Thr Thr Gln Ala
1               5                   10                  15

Leu Gln Leu Phe Leu Arg Ala Thr Thr Glu Pro Arg Thr Phe Ser Ile
            20                  25                  30

Leu Asn Arg Lys Ala Ile Asp Phe Leu Leu Gln Arg
        35                  40


<210> SEQ ID NO 13
<211> LENGTH: 676
<212> TYPE: PRT
<213> ORGANISM: Artificial Sequence
<220> FEATURE:
<223> OTHER INFORMATION: EBOLA GP STRAIN MAYINGA-76

<400> SEQUENCE: 13

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125
```

-continued

```
Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Val Val Ser Asn Gly Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
        355                 360                 365

Ala Thr Ile Ser Thr Ser Pro Gln Ser Leu Thr Thr Lys Pro Gly Pro
    370                 375                 380

Asp Asn Ser Thr His Asn Thr Pro Val Tyr Lys Leu Asp Ile Ser Glu
385                 390                 395                 400

Ala Thr Gln Val Glu Gln His His Arg Arg Thr Asp Asn Asp Ser Thr
                405                 410                 415

Ala Ser Asp Thr Pro Ser Ala Thr Thr Ala Ala Gly Pro Pro Lys Ala
            420                 425                 430

Glu Asn Thr Asn Thr Ser Lys Ser Thr Asp Phe Leu Asp Pro Ala Thr
        435                 440                 445

Thr Thr Ser Pro Gln Asn His Ser Glu Thr Ala Gly Asn Asn Asn Thr
    450                 455                 460

His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Ile
    530                 535                 540
```

-continued

```
Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675


<210> SEQ ID NO 14
<211> LENGTH: 44
<212> TYPE: PRT
<213> ORGANISM: Artificial Sequence
<220> FEATURE:
<223> OTHER INFORMATION: hinge loop Marburg virus GP

<400> SEQUENCE: 14

Asn Leu Val Cys Arg Leu Arg Arg Leu Ala Asn Gln Thr Ala Lys Ser
1               5                   10                  15

Leu Glu Leu Leu Leu Arg Val Thr Thr Glu Glu Arg Thr Phe Ser Leu
            20                  25                  30

Ile Asn Arg His Ala Ile Asp Phe Leu Leu Ala Arg
        35                  40


<210> SEQ ID NO 15
<211> LENGTH: 44
<212> TYPE: PRT
<213> ORGANISM: Artificial Sequence
<220> FEATURE:
<223> OTHER INFORMATION: mutated hinge loop Marburg GP

<400> SEQUENCE: 15

Asn Leu Val Cys Arg Leu Arg Arg Leu Ala Asn Gln Thr Ala Lys Ser
1               5                   10                  15

Leu Glu Leu Leu Leu Arg Val Thr Pro Glu Glu Arg Thr Phe Ser Leu
            20                  25                  30

Ile Asn Arg His Ala Ile Asp Phe Leu Leu Ala Arg
        35                  40


<210> SEQ ID NO 16
<211> LENGTH: 44
<212> TYPE: PRT
<213> ORGANISM: Artificial Sequence
<220> FEATURE:
<223> OTHER INFORMATION: mutated hinge loop Marburg GP

<400> SEQUENCE: 16

Asn Leu Val Cys Arg Leu Arg Arg Leu Ala Asn Gln Thr Ala Lys Ser
1               5                   10                  15

Leu Glu Leu Leu Leu Arg Val Thr Thr Glu Pro Arg Thr Phe Ser Leu
```

-continued

```
            20                  25                  30

Ile Asn Arg His Ala Ile Asp Phe Leu Leu Ala Arg
        35                  40


<210> SEQ ID NO 17
<211> LENGTH: 681
<212> TYPE: PRT
<213> ORGANISM: Artificial Sequence
<220> FEATURE:
<223> OTHER INFORMATION: MARBURG GP

<400> SEQUENCE: 17

Met Lys Thr Thr Cys Leu Leu Ile Ser Leu Ile Leu Ile Gln Gly Val
1               5                   10                  15

Lys Thr Leu Pro Ile Leu Glu Ile Ala Ser Asn Ile Gln Pro Gln Asn
            20                  25                  30

Val Asp Ser Val Cys Ser Gly Thr Leu Gln Lys Thr Glu Asp Val His
        35                  40                  45

Leu Met Gly Phe Thr Leu Ser Gly Gln Lys Val Ala Asp Ser Pro Leu
    50                  55                  60

Glu Ala Ser Lys Arg Trp Ala Phe Arg Ala Gly Val Pro Pro Lys Asn
65                  70                  75                  80

Val Glu Tyr Thr Glu Gly Glu Glu Ala Lys Thr Cys Tyr Asn Ile Ser
                85                  90                  95

Val Thr Asp Pro Ser Gly Lys Ser Leu Leu Leu Asp Pro Pro Thr Asn
            100                 105                 110

Ile Arg Asp Tyr Pro Lys Cys Lys Thr Ile His His Ile Gln Gly Gln
        115                 120                 125

Asn Pro His Ala Gln Gly Ile Ala Leu His Leu Trp Gly Ala Phe Phe
    130                 135                 140

Leu Tyr Asp Arg Ile Ala Ser Thr Thr Met Tyr Arg Gly Lys Val Phe
145                 150                 155                 160

Thr Glu Gly Asn Ile Ala Ala Met Ile Val Asn Lys Thr Val His Lys
                165                 170                 175

Met Ile Phe Ser Arg Gln Gly Gln Gly Tyr Arg His Met Asn Leu Thr
            180                 185                 190

Ser Thr Asn Lys Tyr Trp Thr Ser Ser Asn Gly Thr Gln Thr Asn Asp
        195                 200                 205

Thr Gly Cys Phe Gly Thr Leu Gln Glu Tyr Asn Ser Thr Lys Asn Gln
    210                 215                 220

Thr Cys Ala Pro Ser Lys Lys Pro Leu Pro Leu Pro Thr Ala His Pro
225                 230                 235                 240

Glu Val Lys Leu Thr Ser Thr Ser Thr Asp Ala Thr Lys Leu Asn Thr
                245                 250                 255

Thr Asp Pro Asn Ser Asp Asp Glu Asp Leu Thr Thr Ser Gly Ser Gly
            260                 265                 270

Ser Gly Glu Gln Glu Pro Tyr Thr Thr Ser Asp Ala Ala Thr Lys Gln
        275                 280                 285

Gly Leu Ser Ser Thr Met Pro Pro Thr Pro Ser Pro Gln Pro Ser Thr
    290                 295                 300

Pro Gln Gln Gly Gly Asn Asn Thr Asn His Ser Gln Gly Val Val Thr
305                 310                 315                 320

Glu Pro Gly Lys Thr Asn Thr Thr Ala Gln Pro Ser Met Pro Pro His
                325                 330                 335

Asn Thr Thr Thr Ile Ser Thr Asn Asn Thr Ser Lys His Asn Leu Ser
```

```
            340                 345                 350

Thr Pro Ser Val Pro Ile Gln Asn Ala Thr Asn Tyr Asn Thr Gln Ser
        355                 360                 365

Thr Ala Pro Glu Asn Glu Gln Thr Ser Ala Pro Ser Lys Thr Thr Leu
    370                 375                 380

Leu Pro Thr Glu Asn Pro Thr Thr Ala Lys Ser Thr Asn Ser Thr Lys
385                 390                 395                 400

Ser Pro Thr Thr Thr Val Pro Asn Thr Thr Asn Lys Tyr Ser Thr Ser
                405                 410                 415

Pro Ser Pro Thr Pro Asn Ser Thr Ala Gln His Leu Val Tyr Phe Arg
            420                 425                 430

Arg Lys Arg Asn Ile Leu Trp Arg Glu Gly Asp Met Phe Pro Phe Leu
        435                 440                 445

Asp Gly Leu Ile Asn Ala Pro Ile Asp Phe Asp Pro Val Pro Asn Thr
    450                 455                 460

Lys Thr Ile Phe Asp Glu Ser Ser Ser Ser Gly Ala Ser Ala Glu Glu
465                 470                 475                 480

Asp Gln His Ala Ser Pro Asn Ile Ser Leu Thr Leu Ser Tyr Phe Pro
                485                 490                 495

Lys Val Asn Glu Asn Thr Ala His Ser Gly Glu Asn Glu Asn Asp Cys
            500                 505                 510

Asp Ala Glu Leu Arg Ile Trp Ser Val Gln Glu Asp Asp Leu Ala Ala
        515                 520                 525

Gly Leu Ser Trp Ile Pro Phe Phe Gly Pro Gly Ile Glu Gly Leu Tyr
    530                 535                 540

Thr Ala Gly Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Leu Arg Val
                565                 570                 575

Thr Thr Glu Glu Arg Thr Phe Ser Leu Ile Asn Arg His Ala Ile Asp
            580                 585                 590

Phe Leu Leu Ala Arg Trp Gly Gly Thr Cys Lys Val Leu Gly Pro Asp
        595                 600                 605

Cys Cys Ile Gly Ile Glu Asp Leu Ser Arg Asn Ile Ser Glu Gln Ile
    610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
                645                 650                 655

Ile Leu Leu Leu Leu Ser Ile Ala Val Leu Ile Ala Leu Ser Cys Ile
            660                 665                 670

Cys Arg Ile Phe Thr Lys Tyr Ile Gly
        675                 680


<210> SEQ ID NO 18
<211> LENGTH: 53
<212> TYPE: PRT
<213> ORGANISM: Artificial Sequence
<220> FEATURE:
<223> OTHER INFORMATION: hinge loop H1 HA

<400> SEQUENCE: 18

Gln Lys Ser Thr Gln Asn Ala Ile Asn Gly Ile Thr Asn Lys Val Asn
1               5                   10                  15

Ser Val Ile Glu Lys Met Asn Thr Gln Phe Thr Ala Val Gly Lys Glu
```

```
            20                  25                  30

Phe Asn Lys Leu Glu Arg Arg Met Glu Asn Leu Asn Lys Lys Val Asp
        35                  40                  45

Asp Gly Phe Ile Asp
    50


<210> SEQ ID NO 19
<211> LENGTH: 53
<212> TYPE: PRT
<213> ORGANISM: Artificial Sequence
<220> FEATURE:
<223> OTHER INFORMATION: mutated hinge loop H1 HA

<400> SEQUENCE: 19

Gln Lys Ser Thr Gln Asn Ala Ile Asn Gly Ile Thr Asn Lys Val Asn
1               5                   10                  15

Ser Val Ile Glu Lys Met Asn Thr Gln Pro Thr Ala Val Gly Lys Glu
            20                  25                  30

Phe Asn Lys Leu Glu Arg Arg Met Glu Asn Leu Asn Lys Lys Val Asp
        35                  40                  45

Asp Gly Phe Ile Asp
    50


<210> SEQ ID NO 20
<211> LENGTH: 53
<212> TYPE: PRT
<213> ORGANISM: Artificial Sequence
<220> FEATURE:
<223> OTHER INFORMATION: mutated hingfe loop H1 HA

<400> SEQUENCE: 20

Gln Lys Ser Thr Gln Asn Ala Ile Asn Gly Ile Thr Asn Lys Val Asn
1               5                   10                  15

Ser Val Ile Glu Lys Met Asn Thr Gln Phe Thr Ala Val Gly Lys Glu
            20                  25                  30

Phe Asn Lys Pro Glu Arg Arg Met Glu Asn Leu Asn Lys Lys Val Asp
        35                  40                  45

Asp Gly Phe Ile Asp
    50


<210> SEQ ID NO 21
<211> LENGTH: 565
<212> TYPE: PRT
<213> ORGANISM: Artificial Sequence
<220> FEATURE:
<223> OTHER INFORMATION: Hemagglutinin Influenza A virus (group
      1)(A/Brisbane/59/2007(H1N1)

<400> SEQUENCE: 21

Met Lys Val Lys Leu Leu Val Leu Leu Cys Thr Phe Thr Ala Thr Tyr
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asn Ser His Asn Gly Lys Leu Cys Leu Leu Lys Gly Ile
    50                  55                  60

Ala Pro Leu Gln Leu Gly Asn Cys Ser Val Ala Gly Trp Ile Leu Gly
65                  70                  75                  80

Asn Pro Glu Cys Glu Leu Leu Ile Ser Lys Glu Ser Trp Ser Tyr Ile
```

-continued

```
                85                  90                  95

Val Glu Lys Pro Asn Pro Glu Asn Gly Thr Cys Tyr Pro Gly His Phe
            100                 105                 110

Ala Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Thr
    130                 135                 140

Val Thr Gly Val Ser Ala Ser Cys Ser His Asn Gly Glu Ser Ser Phe
145                 150                 155                 160

Tyr Arg Asn Leu Leu Trp Leu Thr Gly Lys Asn Gly Leu Tyr Pro Asn
                165                 170                 175

Leu Ser Lys Ser Tyr Ala Asn Asn Lys Glu Lys Glu Val Leu Val Leu
            180                 185                 190

Trp Gly Val His His Pro Pro Asn Ile Gly Asn Gln Lys Ala Leu Tyr
        195                 200                 205

His Thr Glu Asn Ala Tyr Val Ser Val Val Ser Ser His Tyr Ser Arg
    210                 215                 220

Lys Phe Thr Pro Glu Ile Ala Lys Arg Pro Lys Val Arg Asp Gln Glu
225                 230                 235                 240

Gly Arg Ile Asn Tyr Tyr Trp Thr Leu Leu Glu Pro Gly Asp Thr Ile
                245                 250                 255

Ile Phe Glu Ala Asn Gly Asn Leu Ile Ala Pro Arg Tyr Ala Phe Ala
            260                 265                 270

Leu Ser Arg Gly Phe Gly Ser Gly Ile Ile Asn Ser Asn Ala Pro Met
        275                 280                 285

Asp Lys Cys Asp Ala Lys Cys Gln Thr Pro Gln Gly Ala Ile Asn Ser
    290                 295                 300

Ser Leu Pro Phe Gln Asn Val His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Val Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Ser Val Ile Glu
385                 390                 395                 400

Lys Met Asn Thr Gln Phe Thr Ala Val Gly Lys Glu Phe Asn Lys Leu
                405                 410                 415

Glu Arg Arg Met Glu Asn Leu Asn Lys Lys Val Asp Asp Gly Phe Ile
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asn Asp Glu Cys Met Glu Ser Val Lys
                485                 490                 495

Asn Gly Thr Tyr Asp Tyr Pro Lys Tyr Ser Glu Glu Ser Lys Leu Asn
            500                 505                 510
```

-continued

Arg Glu Lys Ile Asp Gly Val Lys Leu Glu Ser Met Gly Val Tyr Gln
515 520 525

Ile Leu Ala Ile Tyr Ser Thr Val Ala Ser Ser Leu Val Leu Leu Val
530 535 540

Ser Leu Gly Ala Ile Ser Phe Trp Met Cys Ser Asn Gly Ser Leu Gln
545 550 555 560

Cys Arg Ile Cys Ile
565

<210> SEQ ID NO 22
<211> LENGTH: 52
<212> TYPE: PRT
<213> ORGANISM: Artificial Sequence
<220> FEATURE:
<223> OTHER INFORMATION: hinge loop H3 HA

<400> SEQUENCE: 22

Lys Ser Thr Gln Ala Ala Ile Asn Gln Ile Asn Gly Lys Leu Asn Arg
1 5 10 15

Leu Ile Gly Lys Thr Asn Glu Lys Phe His Gln Ile Glu Lys Glu Phe
20 25 30

Ser Glu Val Glu Gly Arg Ile Gln Asp Leu Glu Lys Tyr Val Glu Asp
35 40 45

Thr Lys Ile Asp
50

<210> SEQ ID NO 23
<211> LENGTH: 53
<212> TYPE: PRT
<213> ORGANISM: Artificial Sequence
<220> FEATURE:
<223> OTHER INFORMATION: mutated hinge loop H3 HA

<400> SEQUENCE: 23

Leu Lys Ser Thr Gln Ala Ala Ile Asn Gln Ile Asn Gly Lys Leu Asn
1 5 10 15

Arg Leu Ile Gly Lys Thr Asn Glu Lys Pro His Gln Ile Glu Lys Glu
20 25 30

Phe Ser Glu Val Glu Gly Arg Ile Gln Asp Leu Glu Lys Tyr Val Glu
35 40 45

Asp Thr Lys Ile Asp
50

<210> SEQ ID NO 24
<211> LENGTH: 53
<212> TYPE: PRT
<213> ORGANISM: Artificial Sequence
<220> FEATURE:
<223> OTHER INFORMATION: mutated hinge loop H3 HA

<400> SEQUENCE: 24

Leu Lys Ser Thr Gln Ala Ala Ile Asn Gln Ile Asn Gly Lys Leu Asn
1 5 10 15

Arg Leu Ile Gly Lys Thr Asn Glu Lys Phe His Gln Ile Glu Lys Glu
20 25 30

Phe Ser Glu Pro Glu Gly Arg Ile Gln Asp Leu Glu Lys Tyr Val Glu
35 40 45

Asp Thr Lys Ile Asp
50

<210> SEQ ID NO 25
<211> LENGTH: 503
<212> TYPE: PRT
<213> ORGANISM: Artificial Sequence
<220> FEATURE:
<223> OTHER INFORMATION: Hemagglutinin Influenza A virus
(group 2)K7N5L2_9INFA

<400> SEQUENCE: 25

```
Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Gly Ile Cys Asp Ser Pro His Gln Ile Leu Asp Gly Glu Asn Cys
    50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
        115                 120                 125

Gly Val Thr Gln Asn Gly Thr Ser Ser Ala Cys Lys Arg Arg Ser Asn
    130                 135                 140

Asn Ser Phe Phe Ser Arg Leu Asn Trp Leu Thr His Leu Lys Phe Lys
145                 150                 155                 160

Tyr Pro Ala Leu Asn Val Thr Met Pro Asn Asn Glu Lys Phe Asp Lys
                165                 170                 175

Leu Tyr Ile Trp Gly Val His His Pro Gly Thr Asp Asn Asp Gln Ile
            180                 185                 190

Ser Leu Tyr Ala Gln Ala Ser Gly Arg Ile Thr Val Ser Thr Lys Arg
        195                 200                 205

Ser Gln Gln Thr Val Ile Pro Asn Ile Gly Ser Arg Pro Arg Val Arg
    210                 215                 220

Asp Ile Pro Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Asn Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr Gln Gly Ile Phe Gly Ala Ile Ala
                325                 330                 335

Gly Phe Ile Glu Asn Gly Trp Glu Gly Met Val Asp Gly Trp Tyr Gly
            340                 345                 350

Phe Arg His Gln Asn Ser Glu Gly Ile Gly Gln Ala Ala Asp Leu Lys
        355                 360                 365
```

Ser Thr Gln Ala Ala Ile Asn Gln Ile Asn Gly Lys Leu Asn Arg Leu
    370                 375                 380

Ile Gly Lys Thr Asn Glu Lys Phe His Gln Ile Glu Lys Glu Phe Ser
385                 390                 395                 400

Glu Val Glu Gly Arg Ile Gln Asp Leu Glu Lys Tyr Val Glu Asp Thr
                405                 410                 415

Lys Ile Asp Leu Trp Ser Tyr Asn Ala Glu Leu Leu Val Ala Leu Glu
            420                 425                 430

Asn Gln His Thr Ile Asp Leu Thr Asp Ser Glu Met Asn Lys Leu Phe
        435                 440                 445

Glu Arg Thr Lys Lys Gln Leu Arg Glu Asn Ala Glu Asp Met Gly Asn
    450                 455                 460

Gly Cys Phe Lys Ile Tyr His Lys Cys Asp Asn Ala Cys Ile Gly Ser
465                 470                 475                 480

Ile Arg Asn Gly Thr Tyr Asp His Asp Val Tyr Arg Asp Glu Ala Leu
                485                 490                 495

Asn Asn Arg Phe Gln Ile Lys
            500

<210> SEQ ID NO 26
<211> LENGTH: 52
<212> TYPE: PRT
<213> ORGANISM: Artificial Sequence
<220> FEATURE:
<223> OTHER INFORMATION: hinge loop influenza B HA

<400> SEQUENCE: 26

Leu Lys Ser Thr Gln Glu Ala Ile Asn Lys Ile Thr Lys Asn Leu Asn
1               5                   10                  15

Ser Leu Glu Leu Glu Val Lys Asn Leu Gln Arg Leu Ser Gly Ala Met
            20                  25                  30

Asp Glu Leu His Asn Glu Ile Leu Glu Leu Asp Glu Lys Val Asp Asp
        35                  40                  45

Leu Arg Ala Asp
    50

<210> SEQ ID NO 27
<211> LENGTH: 52
<212> TYPE: PRT
<213> ORGANISM: Artificial Sequence
<220> FEATURE:
<223> OTHER INFORMATION: mutated hinge loop influenza B HA

<400> SEQUENCE: 27

Leu Lys Ser Thr Gln Glu Ala Ile Asn Lys Ile Thr Lys Asn Leu Asn
1               5                   10                  15

Ser Leu Glu Leu Glu Val Lys Asn Pro Gln Arg Leu Ser Gly Ala Met
            20                  25                  30

Asp Glu Leu His Asn Glu Ile Leu Glu Leu Asp Glu Lys Val Asp Asp
        35                  40                  45

Leu Arg Ala Asp
    50

<210> SEQ ID NO 28
<211> LENGTH: 52
<212> TYPE: PRT
<213> ORGANISM: Artificial Sequence
<220> FEATURE:
<223> OTHER INFORMATION: mutated hinge loop influenza B HA

<400> SEQUENCE: 28

```
Leu Lys Ser Thr Gln Glu Ala Ile Asn Lys Ile Thr Lys Asn Leu Asn
1               5                   10                  15

Ser Leu Glu Leu Glu Val Lys Asn Leu Gln Arg Leu Ser Gly Ala Met
            20                  25                  30

Asp Glu Pro His Asn Glu Ile Leu Glu Leu Asp Glu Lys Val Asp Asp
        35                  40                  45

Leu Arg Ala Asp
    50
```

<210> SEQ ID NO 29
<211> LENGTH: 584
<212> TYPE: PRT
<213> ORGANISM: Artificial Sequence
<220> FEATURE:
<223> OTHER INFORMATION: Hemagglutinin Influenza B virus (B/Yamanashi/166/1998)

<400> SEQUENCE: 29

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Lys Thr
    50                  55                  60

Arg Gly Lys Leu Cys Pro Thr Cys Leu Asn Cys Thr Asp Leu Asp Val
65                  70                  75                  80

Ala Leu Gly Arg Pro Met Cys Val Gly Val Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Lys Ile Arg Leu Ser Thr Gln Asn Val Ile Asn Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Arg Ser Gly Phe Phe Ala Thr Met Ala Trp Ala Val Pro
                165                 170                 175

Lys Asp Asn Asn Lys Thr Ala Thr Asn Pro Leu Thr Val Glu Val Pro
            180                 185                 190

His Ile Cys Thr Lys Glu Glu Asp Gln Ile Thr Val Trp Gly Phe His
        195                 200                 205

Ser Asp Asp Lys Thr Gln Met Lys Asn Leu Tyr Gly Asp Ser Asn Pro
    210                 215                 220

Gln Lys Phe Thr Ser Ser Ala Asn Gly Val Thr Thr His Tyr Val Ser
225                 230                 235                 240

Gln Ile Gly Gly Phe Pro Asp Gln Thr Glu Asp Gly Gly Leu Pro Gln
                245                 250                 255

Ser Gly Arg Ile Val Val Asp Tyr Met Val Gln Lys Pro Gly Lys Thr
            260                 265                 270

Gly Thr Ile Val Tyr Gln Arg Gly Ile Leu Leu Pro Gln Lys Val Trp
        275                 280                 285
```

```
Cys Ala Ser Gly Arg Ser Lys Val Ile Lys Gly Ser Leu Pro Leu Ile
    290                 295                 300

Gly Glu Ala Asp Cys Leu His Glu Lys Tyr Gly Gly Leu Asn Lys Ser
305                 310                 315                 320

Lys Pro Tyr Tyr Thr Gly Glu His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
                405                 410                 415

Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Ile Ala Ile Phe Ile Val Tyr Met Ile Ser Arg Asp
                565                 570                 575

Asn Val Ser Cys Ser Ile Cys Leu
            580


<210> SEQ ID NO 30
<211> LENGTH: 41
<212> TYPE: PRT
<213> ORGANISM: Artificial Sequence
<220> FEATURE:
<223> OTHER INFORMATION: hinge loop HIV-2 env

<400> SEQUENCE: 30

Gln Ser Arg Thr Leu Leu Ala Gly Ile Val Gln Gln Gln Gln Gln Leu
1               5                   10                  15

Leu Asp Ala Val Lys Arg Gln Gln Glu Leu Leu Arg Leu Thr Val Trp
            20                  25                  30

Gly Thr Lys Asn Leu Gln Ser Arg Val
        35                  40


<210> SEQ ID NO 31
```

<211> LENGTH: 29
<212> TYPE: PRT
<213> ORGANISM: Artificial Sequence
<220> FEATURE:
<223> OTHER INFORMATION: mutated hinge loop HIV-2 env

<400> SEQUENCE: 31

Leu Leu Ala Gly Ile Val Gln Gln Gln Gln Gln Pro Leu Asp Ala Val
1 5 10 15

Lys Arg Gln Gln Glu Leu Leu Arg Leu Thr Val Trp Gly
20 25

<210> SEQ ID NO 32
<211> LENGTH: 29
<212> TYPE: PRT
<213> ORGANISM: Artificial Sequence
<220> FEATURE:
<223> OTHER INFORMATION: mutated hinge loop HIV-2 env

<400> SEQUENCE: 32

Leu Leu Ala Gly Ile Val Gln Gln Gln Gln Gln Leu Pro Asp Ala Val
1 5 10 15

Lys Arg Gln Gln Glu Leu Leu Arg Leu Thr Val Trp Gly
20 25

<210> SEQ ID NO 33
<211> LENGTH: 29
<212> TYPE: PRT
<213> ORGANISM: Artificial Sequence
<220> FEATURE:
<223> OTHER INFORMATION: mutated hinge loop HIV-2 env

<400> SEQUENCE: 33

Leu Leu Ala Gly Ile Val Gln Gln Gln Gln Gln Leu Leu Asp Pro Val
1 5 10 15

Lys Arg Gln Gln Glu Leu Leu Arg Leu Thr Val Trp Gly
20 25

<210> SEQ ID NO 34
<211> LENGTH: 29
<212> TYPE: PRT
<213> ORGANISM: Artificial Sequence
<220> FEATURE:
<223> OTHER INFORMATION: mutated hinge loop HIV-2 env

<400> SEQUENCE: 34

Leu Leu Ala Gly Ile Val Gln Gln Gln Gln Gln Leu Leu Asp Ala Pro
1 5 10 15

Lys Arg Gln Gln Glu Leu Leu Arg Leu Thr Val Trp Gly
20 25

<210> SEQ ID NO 35
<211> LENGTH: 847
<212> TYPE: PRT
<213> ORGANISM: Artificial Sequence
<220> FEATURE:
<223> OTHER INFORMATION: HIV-2 Envelope protein

<400> SEQUENCE: 35

Met Ala His Ile Asn Ser His Leu Leu Ile Ser Leu Leu Leu Ile Ser
1 5 10 15

Val Tyr Gly Cys Met Cys Lys Gln Tyr Val Thr Val Phe Tyr Gly Ile
20 25 30

Pro Ala Trp Arg Asn Ala Thr Val Pro Leu Phe Cys Ala Thr Ala Asn

-continued

```
        35                  40                  45

Arg Asp Thr Trp Gly Thr Val Gln Cys Leu Pro Asp Ser Gly Asp Tyr
    50                  55                  60

Thr Glu Ile Ser Val Asn Ile Thr Glu Ala Phe Asp Ala Trp Asn Asn
65                  70                  75                  80

Thr Val Thr Glu Gln Ala Val Asp Asp Val Trp Asn Leu Phe Glu Thr
                85                  90                  95

Ser Leu Lys Pro Cys Val Lys Leu Thr Pro Leu Cys Val Ala Met Asn
            100                 105                 110

Cys Ser Thr Asn Asn Thr Arg Thr Asn Asn Thr Thr Ala Ser Thr Thr
        115                 120                 125

Thr Gly Asn Ser Thr Thr Pro Ile Val Val Asn Glu Ala Ile Pro Cys
    130                 135                 140

Val Lys Ala Asn Asn Cys Ser Gly Ile Gly Leu Glu Asp Val Val Asn
145                 150                 155                 160

Cys Thr Phe Asn Met Thr Gly Leu Arg Gln Asp Glu Arg Lys Gln Tyr
                165                 170                 175

Asn Asp Thr Trp Tyr Arg Arg Asp Leu Glu Cys Glu Gly Thr Arg Cys
            180                 185                 190

Tyr Met Arg Thr Cys Asn Thr Ser Val Ile Gln Glu Ser Cys Asp Lys
        195                 200                 205

His Tyr Trp Asp Ser Leu Arg Phe Arg Tyr Cys Ala Pro Pro Gly Tyr
    210                 215                 220

Ala Ile Leu Arg Cys Asn Asp Thr Asn Tyr Ser Gly Phe Met His Asn
225                 230                 235                 240

Cys Ser Lys Val Val Val Ser Ser Cys Thr Arg Met Met Glu Thr Gln
                245                 250                 255

Thr Ser Thr Trp Phe Gly Phe Asn Gly Thr Arg Ala Glu Asn Arg Thr
            260                 265                 270

Tyr Met Tyr Trp His Gly Arg Asp Asn Arg Thr Ile Ile Ser Leu Asn
        275                 280                 285

Arg Tyr Tyr Asn Leu Thr Met His Cys Arg Arg Pro Gly Asn Lys Thr
    290                 295                 300

Val Leu Pro Ile Thr Ile Met Ser Gly Arg Arg Phe His Ser Arg Pro
305                 310                 315                 320

Val Ile Asn Glu Arg Pro Arg Gln Ala Trp Cys Trp Phe Glu Gly Asn
                325                 330                 335

Trp Thr Glu Ala Met Arg Glu Val Lys Glu Thr Val Met Lys His Pro
            340                 345                 350

Arg Tyr Thr Gly Ile Lys Asn Ile Thr Lys Ile Asn Leu Val Gly Pro
        355                 360                 365

Ser Ala Gly Ser Asp Pro Glu Ala Arg Tyr Met Trp Thr Asn Cys Arg
    370                 375                 380

Gly Glu Phe Phe Tyr Cys Asn Met Thr Trp Phe Leu Asn Trp Val Glu
385                 390                 395                 400

Gly Lys Asn Gly Thr Lys Arg Asn Tyr Val Pro Cys His Ile Arg Gln
                405                 410                 415

Ile Val Asn Thr Trp His Lys Val Gly Lys Tyr Val Tyr Leu Pro Pro
            420                 425                 430

Arg Glu Gly Leu Leu Ser Cys Asn Ser Thr Val Thr Ser Ile Ile Ala
        435                 440                 445

Asn Ile Glu Trp Ile Asp Ser Asn Glu Thr Asn Ile Thr Met Ser Ala
    450                 455                 460
```

-continued

```
Glu Val Gly Glu Leu Tyr Arg Leu Glu Leu Gly Asp Tyr Lys Leu Val
465                 470                 475                 480

Glu Ile Thr Pro Ile Gly Phe Ala Pro Thr Asn Ile Lys Arg Tyr Ser
                485                 490                 495

Ser Ala Thr Pro Arg Asn Arg Arg Gly Val Met Val Leu Gly Phe Leu
            500                 505                 510

Gly Phe Leu Ala Thr Ala Gly Ser Ala Met Gly Ala Ala Ser Leu Thr
        515                 520                 525

Leu Ser Ala Gln Ser Arg Thr Leu Leu Ala Gly Ile Val Gln Gln Gln
    530                 535                 540

Gln Gln Leu Leu Asp Ala Val Lys Arg Gln Gln Glu Leu Leu Arg Leu
545                 550                 555                 560

Thr Val Trp Gly Thr Lys Asn Leu Gln Ser Arg Val Thr Ala Ile Glu
                565                 570                 575

Lys Tyr Leu Lys Asp Gln Ala Leu Leu Asn Ser Trp Gly Cys Ala Phe
            580                 585                 590

Arg Gln Val Cys His Thr Thr Val Pro Trp Pro Asn Glu Ser Leu Thr
        595                 600                 605

Pro Asn Trp Thr Asp Met Thr Trp Gln Gln Trp Glu Glu Lys Val His
    610                 615                 620

Tyr Leu Asp Ala Asn Ile Thr Gln Leu Leu Glu Glu Ala Gln Ile Gln
625                 630                 635                 640

Gln Glu Lys Asn Met Tyr Glu Leu Gln Lys Leu Asn His Trp Asp Val
                645                 650                 655

Phe Ser Asn Trp Phe Asp Phe Thr Ser Trp Met Ala Tyr Ile Arg Leu
            660                 665                 670

Gly Leu Tyr Val Val Val Gly Leu Ile Val Leu Arg Ile Val Ile Tyr
        675                 680                 685

Val Ile Gln Met Leu Ala Arg Leu Arg Lys Gly Tyr Arg Pro Val Phe
    690                 695                 700

Ser Ser Pro Pro Ser Tyr Thr Gln Gln Ile Pro Ile His Lys His Arg
705                 710                 715                 720

Gly Gln Pro Ala Asn Glu Glu Thr Glu Asp Glu Gly Gly Arg Glu Gly
                725                 730                 735

Asp Tyr Arg Ser Trp Pro Trp Gln Ile Glu Tyr Ala His Phe Leu Ile
            740                 745                 750

Arg Gln Leu Arg Asn Leu Leu Ile Trp Leu Tyr Asn Gly Cys Arg Asn
        755                 760                 765

Leu Leu Leu Arg Thr Ser Gln Ile Leu Gln Pro Ala Leu Gln Pro Leu
    770                 775                 780

Arg Leu Ser Leu Ala Tyr Leu Gln Tyr Gly Ile Ser Trp Leu Gln Glu
785                 790                 795                 800

Ala Ile Gln Ala Ala Thr Arg Ala Ala Gly Glu Thr Leu Ala Asn Ala
                805                 810                 815

Gly Arg Ala Leu Trp Glu Ala Leu Arg Arg Thr Ala Gly Ala Ile Ile
            820                 825                 830

Ala Val Pro Arg Arg Ile Arg Gln Gly Leu Glu Leu Ala Leu Leu
        835                 840                 845
```